US005855881A

United States Patent [19]
Loike et al.

[11] Patent Number: 5,855,881
[45] Date of Patent: Jan. 5, 1999

[54] MAMMALIAN ALCOHOL DEHYDROGENASE AND ALDEHYDE DEHYDROGENASE PRODUCTION IN PLANTS

[76] Inventors: John D. Loike, 179-20 Tudor Rd., Jamaica, N.Y. 11432; Suzanne Hickman, 499 Fort Washington Ave., New York, N.Y. 10033; David Holzer, 545 W. 37th St., Miami Beach, Fla. 33140

[21] Appl. No.: 565,447

[22] Filed: Feb. 22, 1996

[51] Int. Cl.$^6$ .............................. A61K 38/54; C12N 9/06; A01H 1/04
[52] U.S. Cl. ............................ 424/94.2; 435/190; 514/2; 800/205
[58] Field of Search ................................ 435/190; 514/2, 514/12; 424/94.2; 800/205

[56] References Cited

U.S. PATENT DOCUMENTS

| | | | |
|---|---|---|---|
| 4,956,282 | 9/1990 | Goodman et al. | 435/69.51 |
| 5,188,958 | 2/1993 | Moloney et al. | 800/205 |
| 5,202,422 | 4/1993 | Hiatt et al. | 530/387.3 |
| 5,384,253 | 1/1995 | Krzyzek et al. | 435/172.3 |

OTHER PUBLICATIONS

Gordon–Kamm, et al., Transformation of Maize Cells and Regeneration of Fertile Transgenic Plants. The Plant Cell, vol. 2, pp. 603–618 (Jul., 1990).
Satre, et al. The Complete Structure of Human Class IV Alcohol Dehydrogenase (Retinol Dehydrogenase) Determined from the ADH7 Gene. The Journal of Biological Chemistry, vol. 269, No. 22, pp. 15606–15612 (Jun. 3, 1994).
Tin et al. Biochem. Genet. 26:343–360 (1988).
Enrique Baraona et al., Life Sciences, vol. 49, pp. 1929–1934 (1991).
Jaume Farrés et al., Enzymology and Molecular Biology of Carbonyl Metabolism 5, Edited by H. Weiner et al., Plenum Press, New York, 1995, pp 331–339.
Eighth Special Report to the U.S. Congress on Alcohol and Health, From the Secretary of Health and Human Services, Sep. 1993, pp. 147–164.
H. Wade Schlameus, Microencapsulation, Southwest Research Institute, San Antonio, Texas.
Alberto Moreno et al., Journal of Biology Chem. 266(2):1128–1133 (1991).
Shozo Yokoyama et al., FEBS Letters 351:411–415 (1991).
Xavier Parés et al., FEBS Letters, 303(1):69–72 (1992).
Brenda Cheung et al., Alcoholism: Clinical and Experimental Research, vol. 19, No. 1, pp. 185–186 (1995).
Xavier Parés et al., Proc. Natl. Acad. Sci. USA, vol. 91, pp. 1893–1897, Mar. 1994.
Alberto Moreno et al., Alcohol & Alcoholism, vol. 29, No. 6, pp. 663–671, 1994.
Jaume Farrés et al., Eur. J. Biochem, 224: 549–557 (1994).
Hirokazu Yokoyama et al., Biochemical and Biophysical Research Communications, vol. 203, No. 1, pp. 219–224 (1994).

Michael A. Satre et al., The Journal of Biological Chemistry, vol. 269, No. 22, pp. 15606–15612 (1994).
Natalia Y. Kedishvili et al., The Journal of Biological Chemistry, vol. 270, No. 8, pp. 3625–3630 (1995).
Natalia Y. Kedishvili et al., Enzymology and Molecular Biology of Carbonyl Metabolism 5, Edited by H. Weiner et al., Plenum Press, New York, 1995, pp. 341–347.
I.P. Maly et al., Histochemistry, 98: 311–315 (1992).
D.M. Pestalozzi et al., Gastroenterology, 85:1011–6 (1983).
Martin R. Wales et al., Enzymology and Molecular Biology of Carbonyl Metabolism 3, Edited by H. Weiner et al., Plenum Press, New York, pp. 337–345 (1990).
Mario Frezza et al., New England Journal of Medicine, vol. 322, No. 2, pp. 95–99 (1990).
Lily C. Hsu et al., Proc. Natl. Acad. Sci. USA, vol. 82, pp. 3771–3775 (1985).
Lily C. Hsu et al., Genomics 2, pp. 57–65 (1988).
Lily C. Hsu et al., Genomics 5, pp. 857–865 (1989).
Lily C. Hsu et al., The Journal of Biological Chemistry, vol. 267, No. 5, pp. 3030–3037 (1992).
Valia Dilova et al., J. Pharm. Pharmacol. 45:987–989 (1993).
S. Sehgal et al., J. Microencapsulation, vol. 12, No. 1, pp. 37–47 (1995).
A. Gabizon, Ann. Biol. Clin., 50:811–813 (1993).
Bartel M. van den Berg et al., Electrophoresis, 12, 64–69 (1991).
Y.H. Hui, Encyclopedia of Food Science and Technology, vol. 2, pp. 697–703 (1992).
Thomas D. Hurley et al., The Journal of Biologial Chemistry, vol. 265, No. 27, pp. 16366–16372 (1990).
Serik Omirulleh et al., Plant Molecular Biology 21: 415–428 (1993).
David McElroy et al., Mol Gen Genet 231: 150–160 (1991).
Judy Callis et al., Genes & Development 1:1183–1200 (1987).
Richard A. Jefferson et al., The EMBO Journal, vol. 6, No. 13, pp. 3901–3907 (1987).
Michael Bevan, Nucleic Acids Research, vol. 12, No. 22, pp. 8711–8721 (1984).
Y.H. Hui, Encyclopedia of Food Science and Technology, Vo. 2, pp. 697–702 (1992).
Richard A. Jefferson, Genetic Engineering, vol. 10, pp. 247–263 (1988).

(List continued on next page.)

*Primary Examiner*—John L. LeGuyader

[57] ABSTRACT

Described is a method of producing mammalian ADH in plants and a method of producing mammalian ALDH in plants. The ADH and ALDH is preferably of human origin and preferably human class IV σ ADH and human ALDH2. Mammalian ADH and ALDH is recovered from the plants and packaged with NAD and a suitable buffer as a pill, paste, or food snack. The composition is taken orally or otherwise before engaging in social drinking to prevent or ameliorate the effects of alcohol consumption.

23 Claims, 5 Drawing Sheets

OTHER PUBLICATIONS

Richard S. Geary, Drug Delivery Systems and Recombinant Proteins, Biotechnology and Safety Assessment edited by J.A. Thomas and L.A. Myers, Raven Press, Ltd., New York, pp. 79–95 (1993).

Ming–Tsair Chan et al., The Journal of Biological Chemistry, Vo. 269, No. 26, 17635–17641, 1994.

Julian K–C. Ma, et al., Eur. J. Immunol. 24: 131–138 (1994).

Masashi Mori et al., FEBS Letters, vol. 336, No. 1, 171–174, Dec. 1993.

Y. Thanavala et al., Natl. Acad. Sci. USA, vol. 92, pp. 3358–3361, Apr. 1995.

Thomas H. Turpen et al., Bio/Technology, vol. 13, pp. 53–57, Jan. 1995.

K. Herbers et al., Bio/Technology, vol. 13, pp. 63–66, Jan. 1995.

Hugh S. Mason et al., Proc. Natl. Acad. Sci. USA, vol. 89, pp. 11745–11749, Dec. 1992.

Philip N. Benfey et al., The EMBO Journal vol. 8, No. 8, pp. 2195–2202, 1989.

Philip N. Benfey et al., Science, vol. 250, 959–966 (1990).

Kathleen D'Halluin et al., The Plant Cell, vol. 4, pp. 1495–1505, Dec. 1992.

D.R. Duncan et al., Planta, 165:322–332 (1985).

C.H. Shaw et al., Nucleic Acids Research, vol. 12, No. 20 pp. 7831–7846 (1984).

Stephen L. Dellaporta et al., Version II, Plant Molecular Biology Reporter, vol. 1, No. 4, pp. 19–21 (1983).

K.J. Pauite et al., Plant Cell Reports, vol. 4, No. 5 pp. 274–276 (1985).

Theodore M. Klein et al., Plant Physiology, vol. 91, No. 1 pp. 440–444 (1989).

T.K. Hodges et al., Biotechnology, vol. 4, pp. 219–223 (1986).

Plant Regeneration in Tissue Cultures of Maize, C.E. Green & C.A. Rhodes, in Maize Biologyical Research (Plant Molecular Biology Assn., Charlottsville, VA.) edited by William F. Sheridan, pp. 367–372 (1982).

C. Koncz, The EMBO Journal, vol. 2, No. 9 pp. 1597–1603 (1983).

Huntington Potter et al., Proc. Nat'l. Acad. Sci., U.S.A., vol. 81, 7161–7165 (1984).

A. Depicker et al., Journal of Molecular and Applied Genetics, pp. 561–573 (1982).

pZMI | 2E-CaMV35S | ADH | NOST | NOSP | NPT II ------ | NOST |  FIG. 1 pZMI | 2E-CaMV35S | ALDH | NOST | NOSP | NPT II ---- | NOST |  FIG. 2 pZMA2 | 2E-CaMV35S | Act I 5' INTRON | ADH | NOST | NOSP | NPT II ------ | NOST |  FIG. 3 pZMA2 | 2E-CaMV35S | Act I 5' INTRON | ALDH | NOST | NOSP | NPT II ------ | NOST |  FIG. 4

MAMMALIAN ALCOHOL DEHYDROGENASE AND ALDEHYDE DEHYDROGENASE PRODUCTION IN PLANTS

FIELD OF THE INVENTION

This invention relates to plant genetic engineering and more particularly to the expression of foreign proteins in plants and specifically to recombinant gene constructs used to introduce foreign proteins, particularly enzymes, into plants and to transgenic plants and their seeds which express a mammalian, preferably a human, enzyme.

BACKGROUND OF THE INVENTION

The invention disclosed herein employs or may employ some of the subject matter disclosed in commonly-owned U.S. patent Ser. No. 08/429,427 filed on Jul. 19, 1995 titled Collagen Compound Production in Plants. The disclosure of Ser. No. 08/429,427 is incorporated herein by reference.

The consumption of alcohol is rapidly increasing as leisure time increases and economic circumstances improve. Recent studies have shown that ninety percent of all Americans drink beverage alcohol, known chemically as ethanol. Between 40% to 50% of American men have a temporary alcohol-induced problem or display occasional drunkenness. Alcohol abuse by non-dependent persons involves patterns of considerable alcohol consumption associated with negative health consequences and/or impairment in social functioning. At least 10% of men and between 3%–5% of women are alcoholics or alcohol dependent. Alcohol dependence or alcoholism manifests itself in craving, tolerance and physical dependence that interfere with the ability to exercise restraint over drinking. Alcoholics display excessive alcohol consumption surpassing caloric or dietary needs or norms resulting in adverse health, social and economic consequences. Alcohol abuse and alcohol dependence (i.e., alcoholism) are serious worldwide public health problems. The international medical and economic cost of alcohol abuse. dependence and withdrawal are enormous; the social repercussions and psychological damage inflicted as a result of alcohol abuse on individuals, on children born with fetal alcohol syndrome, and on victims of alcohol-related accidental death, homicide and suicide are no less costly.

Ingested orally, ethanol is rapidly absorbed from the gastrointestinal tract into the circulatory system and diffuses readily and uniformly throughout the body's tissues and fluids. About 90% of the absorbed alcohol is metabolized in the liver. Alcohol may induce various toxic effects in the human body. Short term toxic effects include confused consciousness, ataxia, headache, vomiting, facial flushing, tachycardia, and heart palpitations. Long term effects of excessive alcohol intake include liver cirrhosis, alcohol liver disease, neurological abnormalities, depression of the immune system, alcoholic muscle disease, tissue damage, malnutrition weight loss, increased blood pressure and risk of cancer, predisposition to infectious diseases, and gastrointestinal disorders such as bleeding. Even individuals engaged in social drinking may develop lapses in mental impairment while driving or may even develop mild medical problems related to their drinking. For instance, blood alcohol levels between 0.5%–0.15% can cause decreased inhibitions of personality traits, slight visual impairment, slight muscular incoordination and slowing of reaction time (reflexes). Twenty -five percent of this group are clinically intoxicated. R. H. Dreisbach, *Handbook of Poisoning*, Lange Medical Publications, Los Altos, Calif., 1980.

On a biochemical and cellular level, alcohol acts as a continuous depressant of the central nervous system much like a general anesthetic. The apparent stimulation that individuals sense after alcohol ingestion results from the unrestrained activity of various parts of the brain that have been freed from inhibition by the alcohol as alcohol exerts its effects upon those parts of the brain, such as the cortex, involved in the most highly integrated functions. The first mental processes that are affected are those that depend on training and previous experience. In individuals ingesting alcohol, confidence initially abounds, the personality becomes expansive and vivacious and speech may become eloquent and occasionally brilliant. Mood swings are uncontrolled and emotional outbursts are displayed frequently. With respect to motor functions, alcohol affects both sensory and motor functions. Spinal reflexes are initially enhanced because they have been freed from central inhibition. Subsequently, these reflexes are impaired. In addition. intake of alcohol affects the efficacy of many classes of drugs. Drugs that interact negatively with alcohol include analgesic agents, oral hypoglycemic agents, and anticoagulants. Goodman and Gilman, *The Pharmacological Basis of Therapeutics*, McMillan Publishing Co., New York, pp. 137–142 (1990).

The adverse effects of alcohol consumption are due to ethanol, the main ingredient of alcohol. The level of ethanol in the blood is a major correlative factor in determining the adverse effects of alcohol. Ethanol is a weakly charged molecule that moves easily through and across cell membranes and rapidly equilibrates between the blood and tissues. After ingestion, small amounts of ethanol are absorbed from the mucus membranes of the mouth and esophagus into the blood. As the alcohol passes into the stomach, about 10% of the alcohol is absorbed from the stomach into the blood. The remaining alcohol of the digestive tract is absorbed by the small intestine. Once absorbed into the blood supply, a small amount (approximately 10%) is excreted out of the body via the lungs, urine or sweat. The remaining blood alcohol is metabolized by the liver to acetaldehyde by the enzyme alcohol dehydrogenase (ADH). The acetaldehyde is then rapidly converted to acetate/acetic acid in the liver by the enzyme aldehyde dehydrogenase (ALDH). The acetic acid is then converted to carbon dioxide and water. Each of these enzymatic steps requires oxidized nicotinomide adenine dinucleotide (NAD+) as a co-factor.

ADH is necessary in the metabolism of retinol or vitamin A, the production of rhodopsin, a vital protein in vision function, and the production of the male hormone, testosterone. Thus, chronic alcoholics often exhibit night blindness reflecting the lack of vitamin A metabolism. In addition, alcoholics may exhibit sterility and effeminization resulting from the decreased production of testosterone.

Many adverse effects of alcohol consumption may be related to the metabolism of alcohol to acetaldehyde by the liver. If acetaldehyde is formed and not further metabolized to acetate, it may cause liver and other tissue damage and toxicity. Acetaldehyde may also enter the blood stream and travel to the brain where it may block certain neurotransmitter activity causing changes in behavior, memory and motor functions. *Alcoholism—The Biochemical Connection*. Joan Mathews Larson, Ph.D., Willard Books, New York, 1992.

Both environmental and genetic factors influence the rate of alcohol degradation. People vary in their susceptibility to the toxic effects of alcohol due to differences in the biological activities of their ADH and ALDH enzymes. There is general agreement that alcoholism is a multifactorial disorder in which there is a significant genetic component, as illustrated by the twin and adoption studies performed over the past twenty years. Women have higher blood alcohol levels than men after consuming comparable amounts of ethanol. Frezza et al., *N. Engl. J Med.* 233:127–129 (1990). Men with an alcoholic biological parent are more than three times more likely to become alcoholic than are men with non-alcoholic biological parents. Several epidemiological surveys have shown that alcoholism is more prevalent in certain nationalities and racial groups than others. N. S. Cotton, *J. Stud Alcohol* 40:89–116 (1940). Other studies comparing alcoholism in identical versus fraternal twins highlight a genetic determinant. The molecular basis for a predisposition towards alcoholism is thought to be related to the various ways that alcohol is metabolized.

Oriental people respond differently than non-Oriental people to alcohol consumption, due, at least in part, to decreased ALDH activity, as described below. Additional factors may be involved such as the deficiency of σ-ADH in the stomachs of Japanese subjects. Baraona et al., *Life Sciences* 49:1929–1934 (1991).

The human gastric ADH enzyme is complex, with ADHs of classes I, III and IV. Mareno et al., *J. Biol Chem.* 266:1128–1133 (1991). The main form of stomach ADH is a class IV σ-ADH which exhibits an affinity toward ethanol much higher than that of the classical liver enzyme. Class IV σ-ADH can metabolize between 10%–20% of the ethanol ingested. The ability to metabolize ethanol is assessed by measuring both the $K_m$, $V_{max}$ and $k_{cat}$ values of an enzyme. $K_m$, is equal to the substrate concentration (moles/liter) that results in one-half of the numerical maximum velocity ($V_{max}$) of the enzyme. $k_{cat}$ is the maximal catalytic rate. Class IV σ-ADH has an exceptionally high $k_{cat}$ value for ethanol. The $k_{cat}$ value of human class IV σ-ADH is about 1000 at pH 7.5. The $k_{cat}$ value of classical human class I liver ADH is between 54 and 143 depending on isozyme. Thus, σ-ADH processes ethanol about at least 10 to 20 times more efficiently than liver ADH. Current evidence suggests that in individuals consuming relatively high amounts of alcohol, it is the class IV σ-ADH that probably is most responsible for metabolizing ethanol in the stomach.

Alcohol may begin being metabolized immediately upon entering the stomach. Any alcohol not metabolized in the stomach is absorbed from either the stomach or the small intestine and transported to the liver. Ethanol oxidation during this first cycle through the stomach, small intestine and liver is called "first-pass" metabolism.

Human class IV σ-ADH has been detected in the mucosa of the upper digestive tract, specifically in the mouth, esophagus, stomach and in the cornea, but not in liver. Farrés et al., *Eur. J Biochem.* 224, 549–557 (1994). This specific distribution suggests a distinct role for the class IV σ-ADH enzyme, different from that of the hepatic ADH, i.e., it may be responsible, in part, for the first-pass metabolism of ingested ethanol in the stomach prior to its distribution into the systemic circulation.

With alcohol doses relevant to social drinking, stomach ADH acts as a barrier against toxic alcohol blood levels. The activity of stomach ADH correlates with the amount of alcohol metabolized by the stomach. In women, alcoholics, and patients treated with cimetidine, a drug used to treat stomach ulcers, the activity of stomach ADH is significantly reduced and more alcohol is absorbed into the blood. R. Gugler, [Review] *Drug Safety* 10(4):271–280 (1994). Several other drugs, such as aspirin, inhibit the enzymatic activity of stomach ADH. Thus, subjects taking aspirin or cimetidine have increased blood alcohol levels, especially after repeated small drinks, which may result in unexpected impairment to perform complex tasks such as driving. Women under the age of 50 express significantly less activity of stomach ADH than age matched men. In addition, extremely low levels of these enzymes are found in young male alcoholics. Once these alcoholics abstained from alcohol for 2–3 weeks, their levels of stomach ADH returned to normal. Seitz et al., *Gut*, 34(10):1433–7 (1993). These studies concluded that the first-pass metabolism of alcohol is related to the activity of stomach class IV ADH. Similarly, studies by Frezza et al., *N. Engl. J Med.* 322(2):95–99 (1990) show that increased bioavailabilty of ethanol resulting from decreased stomach oxidation of ethanol may contribute to the enhanced vulnerability of women to acute and chronic complications of alcoholism.

BIOCHEMICAL PATHWAYS OF ETHANOL DEGRADATION

The major pathway for the breakdown of ethanol is its oxidation in the liver to acetaldehyde and hydrogen. Human alcohol dehydrogenase (ADH) is the enzyme that catalyzes alcohol (ethanol or ethyl alcohol) oxidation to acetaldehyde via hydrogen transfer from the substrate to the cofactor oxidized nicotinamide adenine dinucleotide (NAD$^+$), resulting in conversion to its reduced form, NADH, in accordance with the following reaction formula:

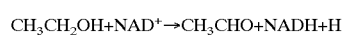

$$CH_3CH_2OH + NAD^+ \rightarrow CH_3CHO + NADH + H$$

ADH also is capable of oxidizing a variety of primary, secondary and tertiary aliphatic alcohols and a limited number of cyclic alcohols to the corresponding aldehydes.

Acetaldehyde is further oxidized to acetate or acetic acid depending on pH, which is then converted to carbon dioxide via the citric acid cycle. Acetate may also undergo reactions to form fatty acids, ketone bodies, amino acids and steroids via its activated form acetyl CoA. Acetate may undergo further metabolism leading, in part, to the production of energy. Aldehyde dehydrogenase (ALDH) is the enzyme which catalyzes the second step in the ethanol metabolic pathway to acetic acid according to the following reaction formula:

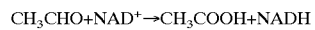

$$CH_3CHO + NAD^+ \rightarrow CH_3COOH + NADH$$

Acetaldehyde oxidation in human liver and other organs is catalyzed by the NAD$^+$-dependent ALDH. The enzyme reaction is irreversible and a wide range of straight-chain and branched-chain aliphatic and aromatic aldehydes serve as substrates producing the corresponding keto acids.

HUMAN ADH

The zinc-containing alcohol dehydrogenases are widely distributed, being found in bacterial, yeast, plants and animals such as reptiles and mammals, and are part of a diverse family. ADH is found in such plants as corn, wheat, barley, rice, potato, petunia, strawberry, clover and peas, among others. Plapp et al, Enzymology & Molecular Biology of Carbonyl Metabolism 4, Vol. 372, Edited by H. Weiner, Plenum Press, New York, pp. 391–400, 1993. The molecular genetics of mammalian ADH has been most frequently studied in humans and most of the human ADH genes have been cloned.

Many bacterial alcohol dehdrogenases have been reported to require zinc for activity, or to contain zinc. Wales, et al., Enzymology & Molecular Biology of Carbonyl Metabolism 3, Edit. H. Weiner et al., Plenum Press, pp. 337–345 (1990). Complete amino acid sequences for bacterial, long-chain, zinc-dependent ADH have been obtained for the NAD-dependent. fermentative ADH from *Alcaligenes eutrophus* (AEADH) (Jendrossek et al., *J. Bacteriol* 170:5248 (1988)), the type 1 NAD-dependent ADH from *Zymomonas mobilis* (ZMADH 1) (Keshav et al., *J Bacteriol.* 172:2491 (1990)) and the NADP-dependent secondary ADH from *Thermoanaerobium brockii* (TBADH) (Peretz et al., *Biochem.* 28:6549 (1989)).

The need for zinc in many enzymes, such as ADH, has significance in growth and repair of vital organs such as the liver. Reductions in the concentration of zinc have been found in liver, red blood cells and plasma in both rats and man following the chronic ingestion of alcohol. While it has not been established that zinc deficiency results in a reduced rate of alcohol metabolism, it has been suggested that other zinc-dependent enzymes may be inhibited by alcohol. Thomson, *Clinics in Endocrinology and Metabolism*, Vol.7, No. 2, pp. 412–417 (1978).

Human ADH is a complex system of enzymes, classes, isozymes and allelic variants. There are at least six basic human genes that code for six different types or isozymes of human ADH characterized according to their electrophoretic migration and kinetic properties as well as their biochemical and immunological properties. ADH classes 1–5 code for the polypeptide α, β, γ, π, and χ forms which combine to form at least eight homo- and heterodimeric enzymes. Class I ADH, with isozymes of α, β, and γ subunits encoded by the $ADH_1$, $ADH_2$ and $ADH_3$ loci. respectively, and class II ADH, with π subunits encoded by the $ADH_4$ locus, are mainly hepatic enzymes and play a key role in ethanol metabolism. In humans, most hepatic ethanol oxidation is performed by Class I ADH and to a lesser degree, by Class II ADH. Class III ADH, with χ subunits encoded by the $ADH_5$ locus, is widely distributed in most organs and is a glutathione-dependent formaldehyde dehydrogenase. Class IV ADH, represented by the isozyme with σ subunits and encoded by the $ADH_7$ locus, is specifically expressed in the stomach and digestive tract organs and has the highest ethanol metabolizing activity of all classes thus far characterized. Moreno et al., *Alcohol and Alcoholism* 29(6):663–671 (1994); Farrés et al., *Eur. J Biochem.* 224, 549–557 (1994). A Class V ADH enzyme encoded by the $ADH_6$ locus has been expressed from a human liver-derived cDNA although the corresponding protein has not been detected or isolated in human tissues. Yasunami, et al., *Proc. Natl. Acad. Sci.*, 88, 7610–7614 (1991): Chen et al., *Biochem. Biophys. Res. Commun.*, 181, 743–747 (1991). Class VI ADH has been recently characterized from deer mouse cDNA. Zheng et al., *J. Biol. Chem.* 268, 24933–34939 (1993).

CLASS IV σ-ADH

Although total ADH activity in human stomach is small (Moreno et al., *J. of Biological Chemistry*, 266, 1128–1133 (1991)), there is evidence that stomach class IV σ-ADH is fully active towards ingested ethanol. Class IV σ-ADH is found in the mucosa of all parts of the human gastrointestinal tract and is particularly localized in the most superficial part of the mucosa where it can be in contact with concentrated ethanol solutions for a prolonged time. Pestalozzi et al., *Gastroenterology* 85:1011–1016 (1983); Maly et al, *Histochemistry* 98:311–315 (1992). The contribution of gastric ADH to total ethanol metabolism is, however, small because of the relatively low amount of class IV ADH present in the gastric mucosa (approximately 10 μg enzyme/g tissue), the small amount of gastrointestinal mucosa as compared to that of liver tissue and the rapid absorption of alcohol into the blood. Pares, Enzymology & Molecular Biology of Carbonyl Metabolism 4, Vol. 372, Edited by H. Weiner, Plenum Press, New York, pp. 475–480, 1993.

Cheung et al., *Alcoholism: Clinical and Experimental Research*, 19(1):185–186 (1995) isolated, cloned, and sequenced a partial human stomach class IV ADH cDNA which contains 222 nucleotides encoding amino acid residues 227–299 of the ADH subunit. The amino acid sequence deduced from this cDNA was highly homologous (81.1% sequence identity) with the rat stomach class IV ADH sequence reported by Pares et al., *Proc. Natl. Acad. Sci.*, 91:1893–1897 (1994).

Class IV σ-ADH isolated from human stomach tissue exhibits a high $K_m$ for ethanol (about 41 mM) and a very high catalytic efficiency ($k_{cat}$ of about 1000–1500 $min^{-1}$) for ethanol oxidation. Moreno et al., *J. Biol. Chem.* 266(2):1128–1133 (1991); Stone et al., *Alcohol. Clin. Exp. Res.* 17:911–918 (1993). Satre et al., *J. Biol. Chem.* 269(22):15606–15612 (1994) report the complete coding nucleotide sequence for the gene encoding human stomach class IV σ-ADH based on an analysis of partial cDNA clones isolated from a human stomach cDNA library and a partial genomic clone isolated from a human genomic library and the deduced full-length amino acid sequence of human Class IV ADH composed of 373 amino acids following the initiator methionine. Analysis of the deduced amino acid sequence of human stomach Class IV ADH indicates that it has 59%–69% sequence identity to the other four human ADH classes. Satre et al., *J. Biol. Chem.* 269, 15606–15612 (1994).

Farrés et al., *Eur. J Biochem.* 224, 549–557 (1994) reported the complete nucleotide sequence of the human class IV σ-ADH cDNA from stomach, assembled from partial cDNA clones and fragments of the cDNA sequences amplified by PCR from a cDNA library, comprising the full coding region and the non-coding regions at the 5' and 3' ends, and its deduced amino acid sequence.

Yokoyama et al., *Biochem. Biophys. Res. Commun.* 203 (1):219–224 (1994), determined the complete structure of human Class IV σ-ADH by molecular cloning of the enzyme's cDNA from a human stomach λgt11 phage library amplified by PCR.

Yokoyama et al., *FEBS Letters* 351:411–415 (1994) reported the isolation and sequence determination of a functional human class IV ADH gene. The gene has 9 exons and 8 introns consistent with the highly conserved intron/exon structure of other mammalian ADH genes. The exons span about 2.2 kb. The predicted amino acid sequence of the exon coding regions indicates that a protein of 373 amino acids, excluding the amino-terminal methionine, would be translated, sharing greater sequence identity with class I ADH (69%) than with classes II, III or V ADH (59–61%). The molecular weight of stomach Class IV ADH is approximately 38,000 which represents a relatively small molecule. In comparison, one chain of collagen I has a molecular weight of about 90.000.

Kedishvili et al., in *J. Biol. Chem.* 270(8):3625–3630 (1995) and in Enzymology & Molecular Biology of Carbonyl Metabolism 5, Edited by H. Weiner, Plenum Press, New York, pp. 341–347. (1995) describe the isolation and complete nucleotide sequence of a cDNA encoding human stomach σ-ADH. To clone the human stomach σ-ADH cDNA, Kedishvili et al. employed a PCR amplification strategy to obtain an 873 base pair PCR product encoding human stomach σ-ADH. A human stomach cDNA library was screened with this PCR product and a full-length 1966-base pair cDNA clone for human stomach class IV σ-ADH was isolated. The cDNA encodes the complete σ-ADH subunit of 373 amino acids with a $M_r$ of 39,902. The 5' end of this cDNA starts with the ATG codon immediately followed by the coding region. The 3'-untranslated region is 825 base pairs long and contains a single polyadenylation signal at nucleotide 1877. The 373 amino acid σ-ADH encoded by this cDNA was expressed in *E. coli*. The deduced amino acid sequence of σ-ADH is identical with that reported by Stone et al., *Alcoholism Clin. Expt. Res.* 17:911–918 (1993).

Hurley et al., *J Biol Chem.* 265(27):16366–16372 (1990) used site-directed mutagenesis to replace Arg-47 of human $\beta_1\beta_1$ ADH with various other amino acids. The mutated enzymes were expressed in *E. coli*. The substitution of Lys, His and Gln at position 47 caused a decrease in affinity for coenzyme and an increase in the $V_{max}$ for ethanol oxidation. Thus, while naturally occurring mammalian ADH is preferred for use in the invention, it is possible to manipulate ADH composition by site directed mutagenesis to improve the efficiency of ethanol metabolism.

HUMAN ALDH

As ethanol is metabolized by the stomach or liver it is first converted to acetaldehyde. Acetaldehyde is then metabolized to acetic acid by the enzyme aldehyde dehydrogenase (ALDH). This enzyme is very important in ethanol metabolism because acetaldehyde is about 10 times more toxic than ethanol. Brein and Loomis, Can. J. Physiology & Pharmacology 61:1–28 (1983). Thus, the direct toxic effects of alcohol and alcohol-related physical alterations have been attributed to acetaldehyde rather than to ethanol itself. Acetaldehyde is chemically very reactive and can form schiff-base adducts with aromatic amines. Current evidence suggests that acetaldehyde causes increased heart rate, cardiac vasoconstriction and hypotension. Besides its role in detoxification and retinal oxidation, there is evidence that ALDH, particularly ALDH1 and ALDH3, functions in anti-tumor drug metabolism and plays a role in resistance to anti-tumor drug toxicity. Yoshida et al., Enzymology & Molecular Biology of Carbonyl Metabolism 4, Vol. 372, Edited by H. Weiner, Plenum Press, New York, pp. 63–72, 1993; Sreerama et al., Enzymology & Molecular Biology of Carbonyl Metabolism 4, Vol. 372, Edited by H. Weiner, Plenum Press, New York, pp. 99–114, 1993.

An inactive dominant mutant form of mitochondrial ALDH2 was discovered by Goedde et al, *Hum. Genet.* 51:331–334 (1979), and shown to be present in approximately 50% of major Asian populations, i.e., approximately 30% of Chinese, 50% of Japanese, 30–50% of Koreans and 50% of Vietnamese express this defective form of ALDH2. H. R. Thomasson et al., *Alcoholism, Clinical & Experimental Research* 18(3):640–643 (1994); Goedde et al., *Human Genetics* 88(3):344–346 (1992). In Americans, about 10% express a defective form of ALDH2. This defective form of liver ALDH2 may be attributed to a single nucleotide exchange resulting in a glutamic acid to lysine substitution at the 14th position from the carboxyl terminus that drastically reduces enzymatic activity and therefore markedly impairs the ability of heterozygous and homozygous individuals to metabolize a variety of aldehydes including acetaldehyde. Yoshida et al, 1984, *Proc. Natl. Acad. Sci. USA* 81:258–261 (1984). Such individuals do not display any pathologic abnormalities but, after ingesting even moderate amounts of alcohol, experience the so-called "alcohol sensitivity symptoms" or "alcohol flush" reaction of facial flushing due to increased blood flow to the earlobes and face, increased heart rate, headaches, heart palpitations, shortening of breath, decreased blood pressure, vertigo, nausea and vomiting, hot feeling in the stomach, and muscle weakness. D. P. Agarwal et al., [Review] *Pharmacogenetics* 2(2):48–62 (1992); Goedde et al., *Phar. Ther.* 45:345–371 (1990). This mutation is considered a negative biological risk factor for alcoholism and appears to have survival value: alcoholism and alcohol abuse virtually do not exist among Asian flushers. When members of this group consume even small amounts of alcoholic beverages they present with facial flush. Y. C. Chao et al., *Hepatology* 19(2):360–366 (1994); D. I. Sherman et al., EXS 71:291–300 (1994); H. R. Thomasson et al., *Alcoholism, Clinical & Experimental Research* 18(3):640–643 (1994).

ALDH isozymes may be distinguished based on their physico-chemical properties, enzyme properties, subcellular and tissue distribution, sequence identities, as well as their chromosomal assignment. There are at least five ALDHs that have been purified and characterized from human liver or stomach: cytosolic ALDH1, mitochondrial ALDH2, ALDH3, ALDH4 (also known as glutamic γ semialdehyde dehydrogenase or GSDH) and γ-aminobutyraldehyde dehydrogenase (GABALDH). Human ALDHs can be divided into two groups: those with high-$K_m$ (mM range) values toward acetaldehyde and those with low-$K_m$ (µM range) values toward acetaldehyde. The low $K_m$ forms comprise ALDH1 ($K_m$=30 µM), ALDH2 ($K_m$=3 µM) and GABALDH ($K_m$=50 µM) which play a major role in the oxidation of toxic acetaldehyde produced from ethanol. The high $K_m$ forms comprise ALDH3 ($K_m$=83 mM), and ALDH4 ($K_m$=5 mM). Yin et al., Enzymology & Molecular Biology of Carbonyl Metabolism 4, Vol. 372, Edited by H. Weiner, Plenum Press, New York, pp. 87–98, 1993.

The distribution of ALDH1 and ALDH2 appears to be ubiquitous in human tissues, with the highest activity in liver, except that ALDH2 is not present in erythrocytes. ALDH2 is found in the mitochondria of the hepatocyte. Human ALDH3 is found in liver, stomach, esophagus, gingiva, lung, cornea and lens, with high activity in stomach, esophagus, and cornea and low activity in liver and lens. ALDH4 occurs in a limited number of tissues and is most abundant in liver and kidney. γ-aminobutyraldehyde dehydrogenase has been purified from liver, and its tissue distribution remains to be clarified. Yin et al., Enzymology & Molecular Biology of Carbonyl Metabolism 4, Vol. 372, Edited by H. Weiner, Plenum Press, New York, pp. 87–98, 1993.

Human ALDH1 and ALDH2 are homotetramers consisting of subunits of 54,000 D. Their amino acid sequences (500-residue polypeptide) have been determined. Hempel et al., *Eur. J Biochem.* 141:21–35 (1984); Hempel et al., *Eur. J Biochem.* 153:13–28 (1985). The cDNAs, genomic clones and genes of human ALDH1 and ALDH2 have been cloned and characterized. Hsu et al., *Proc. Natl. Acad. Sci. USA*, 82:3771–3775 (1985); Hsu et al., *Genomics*, 2:57–65 (1988); Hsu et al., Genomics, 5:857–865 (1989). Both genes consist of 13 exons and introns spanning about 50 kbp in length and are widely distributed among various tissues and generally constitutively expressed.

A partial amino acid sequence of human stomach ALDH3 has been reported. Yin et al., *FEBS Letters,* 283:85–88 (1991). Unlike ALDH1 and ALDH2, ALDH3 has a dimeric structure. The cDNA and gene of human stomach ALDH3 have also been cloned and expressed. Hsu et al., *J Biol. Chem.,* 267(5):3030–3037 (1992). Hsu et al., Enzymology & Molecular Biology of Carbonyl Metabolism 4, Vol. 372, Edited by H. Weiner, Plenum Press, New York, pp. 141–152, (1993) determined the full sequence of the cDNA and the genomic organization of human stomach ALDH3. The full length cDNA is 1624 bp in length. The deduced sequence encodes 453 amino acid residues. The cDNA containing the complete coding region for GABALDH was obtained by Lin et al., *FASB J.* 7:A1297 (1993). One isozyme, ALDH5 (ALDHx), expressed in various tissues including liver, brain, adrenal gland, testis, stomach and parotid gland, has been identified by reverse genetics and found to contain no intron in the coding region. Hsu et al., *J. Biol. Chem.*, 266:12257–12265 (1991). Recently, Hsu et al., Enzymology & Molecular Biology of Carbonyl Metabolism 5, Edited by H. Weiner, Plenum Press, pp. 159–168, 1995, used reverse transcriptase-polymerase chain reaction (RT-PCR) to clone and identify ALDH6 and ALDH7 cDNA from a human salivary gland and a human kidney library, respectively, and isolated an ALDH8 genomic clone during the process of screening for the human ALDH7 genomic clones.

Since the $K_m$ value for acetaldehyde for human ALDH3 is very high, it does not contribute to ethanol metabolism in vivo. ALDH3 has been proposed to be involved in the detoxification of the aldehyde products of lipid peroxidation, and for oxidation of heptaldehyde and benzaldehyde. Yin et al., Enzymology & Molecular Biology of Carbonyl Metabolism 4, Vol. 372, Edited by H. Weiner, Plenum Press, New York, pp. 87–98, 1993; Lindahl et al., *Biochem. Pharmacol.* 41:1583 (1991); Hsu et al., Enzymology & Molecular Biology of Carbonyl Metabolism 4, Vol. 372, Edited by H. Weiner, Plenum Press, New York, pp. 141–152 (1993). There is no evidence that ALDH3 is defective in Asians exhibiting facial flush. ALDH4 is most active for glutamic γ semialdehyde as a substrate.

Mitochondrial ALDH2 is thought to have a major role in acetaldehyde oxidation in vivo because its $K_m$ value is comparable to liver acetaldehyde levels after alcohol administration and Oriental subjects who lack ALDH2 activity exhibit facial flushing. Cytosolic ALDH may also play a role in alcohol metabolism. Hsu et al., *Genomics,* 5:857 865 (1989).

PLANT GENETIC ENGINEERING

Plant genetic engineering techniques are utilized to obtain plants having improved characteristics or traits and to incorporate heterologous genes from a source other than the transformed plant into plant cells to obtain desired traits or to produce useful polypeptides in the plant cells. Thus, transgenic plants have been developed to produce crops of increased value.

Transgenic plants have been developed which produce foreign biological proteins. The 5' regulatory region and putative signal sequence of a rice alpha amylase gene was fused to a bacterial gene encoding β-glucuronidase (GUS) and introduced into rice, tobacco, and potato via Agrobacterium-mediated transformation systems. Expression of alpha amylase was suppressed by the presence of sucrose in the medium and induced by its absence. Ming-Tsair Chan et al., *J. Biol. Chem.* 269:17635–17641 (1994). Turpen et al., *Bio/Technology* 13:53–57 (1995), disclose malarial epitopes expressed on the surface of recombinant tobacco mosaic virus. The authors engineered hybrid virions of tobacco mosaic virus that contain malaria-parasite immunodominant sequences recognized by protective monoclonal antibodies against these parasites and that yet retain their infectivity.

Herbers et al. in *Bio/Technology* 13:63–66 (1995) disclose expression at high levels of a thermostable, microbial xylanase from *Clostridium thermocellum* in the apoplast of transgenic tobacco. The expressed xylanase was easily purified.

Tobacco plants were genetically transformed with the gene encoding hepatitis B surface antigen (HBsAg) linked to a nominally constitutive promoter. The transgenic plants produced HBsAg which is antigenically and physically similar to the HBsAg particles derived from human serum and recombinant yeast. Mason et al., *Proc. Nat. Acad. Sci., USA,* 89:11745–11749 (1992). The immunological response elicited in vivo by using recombinant HBsAg purified from transgenic tobacco leaves was qualitatively similar to that obtained by immunizing mice with yeast-derived recombinant HBsAg (commercial vaccine). Both B- and T-cell epitopes are preserved when the antigen is expressed in transgenic tobacco. Thanavala et al, *Proc. Nat. Acad. Sci. USA,* 92:3358–3361 (1995).

Mori et al. in *FEBS* 13403, vol. 336, no. 1, 171–174 (1993), disclose construction of transgenic tobacco plants expressing viral RNA replication genes of brome mosaic virus (BMV) and BMV RNA3 derivative carrying the human gamma interferon gene.

The genes encoding the heavy and light chains of a mouse monoclonal antibody (mAb Guy's 13) have been cloned and expressed in tobacco plants, Nicotiana tabacum. Transgenic plants were regenerated that secrete full-length Guy's 13 antibody. Antigen binding studies confirmed the fidelity of assembly and demonstrated that the antibody is fully functional. Furthermore, the plant antibodies retained the ability to aggregate streptococci, which confirms that the bivalent antigen-binding capacity of the full length antibodies is intact. The results demonstrate that IgA as well as IgG class antibodies may be assembled correctly in tobacco plants and suggest that transgenic plants may be suitable for high-level expression of more complex genetically engineered immunoglobulin molecules. Ma, et al., *Eur. J. Immunol.* 24:131–138 (1994).

Plant genetic engineering is employed to obtain plants having improved characteristics or traits, such as virus resistance, insect resistance, herbicide resistance, enhanced stability, improved plant taste or nutritional value, altering, starch, oil and protein profile, yield or quality. For instance, work is being done on tomatoes that may be vine-ripened and shipped without bruising, and to provide tomatoes which are better tasting, have improved color and higher vitamin content and which contain more solids. Other projects are directed to generate tomatoes with improved viscosity, i.e., thickness and texture, which means fewer tomatoes are required to generate the same amount of catsup.

Pectin, used to make jelly thicken or gel, occurs naturally in many fruits and vegetables, giving them their firmness. The pectin in ripening tomatoes is degraded by the enzyme polygalacturonase (PG). As pectin is destroyed, the, cell walls of tomatoes break down and soften, making them difficult to successfully ship to market. Reducing the amount of PG in tomatoes slows cell wall breakdown and results in a fruit which remains firm for a longer time at ambient temperature. Calgene, Inc. of Davis, Calif. developed a tomato which incorporates a gene that essentially attaches itself to the PG gene and inactivates it. Such transgenic plants produce drastically reduced levels of PG. This slows the natural softening process that accompanies ripening and allows the Flavr Savr™ tomato to spend more time on the vine than other tomatoes. This results in a more flavorful tomato which is firm enough to be shipped.

U.S. Pat. No. 5,202,422 to Hiatt et al. issued Apr. 13, 1993 discloses a method for producing a glycopolypeptide multimer by introducing first and second mammalian genes encoding the constituent parts of the multimer into first and second respective members of a plant species, generating a progeny from the first and second plant species members, and isolating the glycopolypeptide multimer from the progeny plant.

U.S. Pat. No. 5,188,958 to Moloney et al. issued Feb. 23, 1993 discloses transgenic Brassica species cells (such as rapeseed and rutabaga) produced by transformation of cell cultures with foreign DNA which when expressed will alter the phenotype of the transgenic cells using a manipulated Agrobacterium transformation system followed by regeneration of plants from transformed cells. An example of such foreign DNA is the gene for kanamycin resistance. The cells and the plants produced thereby are capable of expressing the foreign gene.

U.S. Pat. No. 5,384,253 to Krzyzek et al. issued Jan. 24, 1995 discloses a method to increase the susceptibility of cultured Zea mays cells to stable transformation with recombinant DNA via electroporation so that the cells retain their ability to regenerate fertile, transgenic Zea mays plants containing the introduced DNA which may be inherited by progeny of the transformed plant.

D'Halluin et al., Transgenic Maize Plants by Tissue Electroporation, *The Plant Cell*, 4:1495–1505 (1992) describe the production of normal, fertile transgenic monocots by creating transformation-competent cells from immature zygotes and type I callus by gentle partial hydrolysis of certain cell wall components, such as pectin. This results in enhanced permeability of the cell wall to exogenous DNA while not destroying cell viability.

Using transgenic plants to express foreign genes may at times be problematic as plants may not always properly fold or process mammalian proteins and may lack post-translational enzymes that are mammalian specific so as to provide the desired degree of biological or physiological activity in the resulting protein. This is not a concern here as there are no post-translational modifications required for ADH and ALDH to assert their full biological activity.

There is a need to significantly reduce the absorption of alcohol in the blood and to enable social drinkers to be unaffected or minimally affected by alcohol consumption. There is a need to reduce or ameliorate the effects of alcohol consumption in social drinkers and to suppress an urge for alcohol.

There is a need to increase the levels of stomach ADH to enable more ethanol to be metabolized before it enters the blood stream. This is particularly true for Oriental people lacking stomach ADH. Thus, there is a need for a consumable form of stomach ADH available either as a pill paste or as a snack which could be taken orally or otherwise immediately before engaging in social drinking to enable consumers to metabolize greater amounts of ingested alcohol resulting in lower blood alcohol levels. Individuals engaged in social drinking will thus absorb less alcohol into their blood and be less affected by the mental impairments or decreased visual-motor coordination resulting from alcohol ingestion.

There is also a need for ALDH for Oriental people having a defective form of this enzyme.

There is also a need for a composition taken prior to drinking an alcoholic beverage which will counter the effects of alcohol and reduce or eliminate the symptoms of facial flush.

There is therefore a need for a supply of AHD and ALDH which have the biochemical and biophysical properties required for countering the effects of alcohol in the body.

OBJECTS AND SUMMARY OF THE INVENTION

It is an object of the invention to provide a method of producing a ready supply of ADH and/or ALDH from a specific non-mammalian source.

It is an object of the invention to provide a method of inexpensively producing high yields of ADH and/or ALDH in a short period of time.

It is another object of the invention to provide a method of producing ADH and/or ALDH in plants, yeast and bacteria.

It is a further object of the invention to provide a method of producing an inexpensive, ready supply of ADH and/or ALDH for use as a dietary supplement or in effective doses for pharmaceutical/therapeutic applications.

Another object of the invention is to provide a method of producing a ready supply of ADH and/or ALDH by producing ADH and/or ALDH in plants, yeast and bacteria by genetic manipulation.

It is another object of the invention to provide a method of producing a ready supply of ADH and/or ALDH having the biochemical and biophysical properties suitable for use in the dietary supplement or pharmaceutical industries.

A still further object of the invention to provide a gene construct for producing ADH and/or ALDH in plants, yeast and bacteria.

Another object of this invention is the development of transgenic plants and yeasts capable of reproduction which produce ADH and/or ALDH.

Still another object of the present invention is the production of low cost mammalian ADH and/or ALDH in plants, yeast and bacteria.

Yet another object of the invention is to provide a method of easily and inexpensively producing a composition comprising effective amounts of human ADH and ALDH of plant yeast or bacterial origin in combination with NAD for dietary supplement use.

Still another object of the invention is to provide a method of easily and inexpensively producing a composition comprising an effective amount of human ALDH of plant, yeast or bacterial origin in combination with NAD for dietary supplement use.

These and other objects of the invention are accomplished by providing a method of producing transgenic plants capable of expressing mammalian ADH and a method of producing transgenic plants capable of expressing mammalian ALDH. The method comprises introducing a gene construct into cells of a plant. The gene construct comprises a DNA sequence coding for ADH operably linked to an upstream (5') plant promoter sequence capable of initiating and directing transcription in plant cells of the DNA sequence. The gene construct is integrated into the plant genome such that, upon transformation, the plant cells express ADH. Transgenic plants are regenerated from the transformed plant cells and grown for a time and under conditions sufficient to permit expression of ADH. ADH is then recovered from the transgenic plants. A similar method is employed using a gene construct comprising a DNA sequence coding for ALDH to produce transgenic plants capable of expressing ALDH.

In its broadest applications, ADH and ALDH may be of any class or type and from any species. More particularly, ADH is preferably class IV ADH of mammalian and more preferably of human origin. ALDH is preferably ALDH2 of mammalian and more preferably of human origin.

Additionally, in an embodiment of the invention, a gene construct comprises at least a DNA sequence coding for ADH operably linked upstream to an (5') promoter sequence capable of initiating and directing transcription in plant cells of the DNA sequence. When such a gene construct is incorporated into a plant genome, the DNA sequence coding for ADH is expressed in the plant's cells. In a further embodiment of the invention, a similar gene construct comprises at least a DNA sequence coding for ALDH rather than ADH.

In further embodiments of the invention, there is provided an ADH-producing plant cell and an ALDH-producing plant cell produced by the method described above and an ADH producing plant cell and an ALDH producing plant cell descended from the above respective plant cells. In yet other embodiments of the invention, there is provided ADH produced from plants and seeds, ALDH produced from plants and seeds and a pill, food product or the like for oral consumption or for internal administration which includes ADH and ALDH produced from plants.

In other aspects, the invention is directed to plant cells transformed with the gene constructs described above and to plants regenerated from or containing these transformed plant cells. In further aspects, the invention is directed to methods to produce plants and seeds which produce ADH and plants and seeds which produce ALDH, which method comprises cultivation of the transgenic plants of the invention followed by recovery of ADH and/or ALDH. The same plants may produce both ADH and ALDH, but in a preferred embodiment, different plants are used to produce ADH and ALDH.

In yet other aspects, the invention is directed to a composition comprising an effective amount of human ALDH2 in combination with an effective amount of NAD and buffering agent packaged in the form of pills, capsules, powders, pastes and food products. In further aspects, the invention is directed to a composition comprising an effective amount of human class IV σ-ADH and an effective amount of human ALDH2 in combination with an effective amount of NAD and buffering agent packaged in the form of pills, capsules, powders pastes and food products. The human ADH and ALDH is produced from plants, seeds, yeast or bacteria (such as E. coli) and preferably from plants.

The invention contemplates genetically altering plants, preferably corn plants, to program them to synthesize ADH and ALDH of mammalian, and preferably of human origin. The ADH and ALDH producing corn plants are used as an inexpensive method to generate plant derived ADH and ALDH which may be packaged in gelatin coated capsules or pills. The advantage of corn is that it is also the source of corn starch, an essential filler substance used in the pharmaceutical industry in making pills and capsules. An additional advantage of using corn as the transgenic plant is the recovery of ADH and ALDH without added cost as technology is already well developed to extract protein from corn, for instance, by a wet milling process.

The ADH and ALDH that may be produced by the methods of this invention include, for instance, mammalian Class IV ADH and ALDH2; preferably the ADH and ALDH is of human origin. In its broadest applications, the present invention is not limited to any particular species of mammals. For instance, mammals such as swine, goat, sheep, oxen and cattle may be used. Neither is the invention limited to the particular classes of ADH and ALDH described here; any class or type ADH or ALDH may be produced by the method of the invention.

These and other features, objects and advantages of the invention will be apparent from the following description of the preferred embodiment, taken in conjunction with the accompanying drawings and appended claims.

BRIEF DESCRIPTION OF THE DRAWINGS

The invention is illustrated by way of example and not limitation in the Figures of the accompanying drawings in which like references denote like or corresponding parts, and in which:

FIG. 1 shows a schematic representation of a gene construct according to the invention comprising at least a DNA sequence coding for ADH;

FIG. 2 shows a schematic representation of a gene construct according to the invention comprising at least a DNA sequence coding for ALDH;

FIG. 3 shows an alternative schematic representation of a gene construct according to the invention comprising at least a DNA sequence coding for ADH;

FIG. 4 shows an alternative schematic representation of a gene construct according to the invention comprising at least a DNA sequence coding for ALDH;

Figure 5:
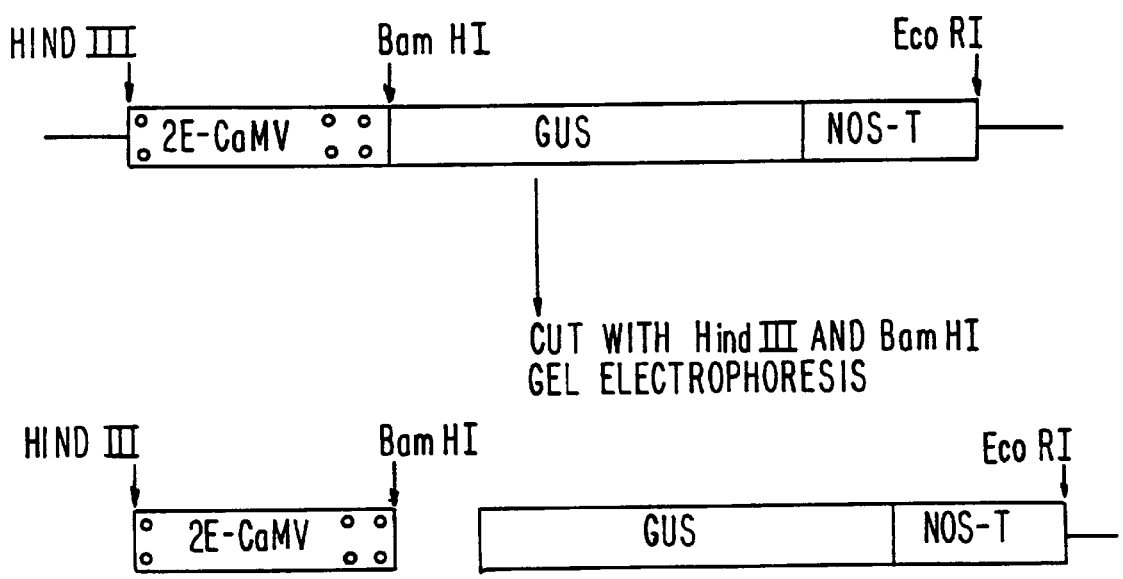
FIG. 5 is a map of plasmid pKM794 where 2E-CaMV is the doubled enhancer-CaMV35S promoter. GUS is the Beta glucuronidase reporter gene and N-T is the nopaline synthase terminator sequence.

The indicated restriction sites in FIGS. 5–8 are abbreviated as follows: Xb, XbaI; N, NcoI, B, BamHI; H. HindIII; Sn, SnaBI; S, SstI and E, EcoRI.

DETAILED DESCRIPTION OF THE PREFERRED EMBODIMENTS

The invention provides a method of producing transgenic plants capable of expressing ADH and a method of producing transgenic plants capable of expressing ALDH. The method comprises introducing a gene construct into cells of a plant. In the case of ADH, the gene construct comprises a DNA sequence coding for ADH operably linked to an upstream (5') to a promoter sequence capable of initiating and directing transcription in plant cells of the DNA sequence. The gene construct is integrated into the plant genome such that upon transformation the plant cells express ADH. Transgenic plants are regenerated from the plant cells which have been transformed and grown for a time and under conditions sufficient to permit expression of ADH. In the case of ALDH, a similar gene construct is employed, with the exception that a DNA sequence coding for ALDH rather than ADH is used.

The present invention is capable of providing an unlimited, low-cost supply of ADH and ALDH. By providing transgenic ADH and ALDH producing plants, there will never be a shortage of raw material. The present invention contemplates producing transgenic plant cells via electroporation or other methods of transformation which are capable of regeneration to yield fertile, transgenic plants which produce ADH and ALDH. Since corn and other plants contain their own form of ADH and ALDH, the introduction of the stomach isoform of ADH or of mammalian ALDH should not affect plant development.

As a result of integration of the gene construct in the plant genome, the gene construct will be present in all or substantially all of the cells of the plant tissue after transformation and regeneration. Alternatively, expression of the ADH and the ALDH genes may be targeted to particular plant tissue or particular stages in the development of the plant, by the use of tissue or organ specific, or developmental stage specific promoters which can be expressed in the plant cell of choice.

Gene constructs are introduced into a plant, preferably corn, which instructs the plant to produce ADH in its cells.

Other gene constructs are introduced into the same, and preferably into different plants to instruct them to produce ALDH in their cells. ADH and ALDH are extracted from corn using known wet milling technology.

Preferably the plant is corn and the ADH or ALDH is synthesized in the corn kernels. It is not efficacious to use the corn form of ADH because it is quite different from that found in human stomach and does not express the high ethanol turnover of stomach ADH. Much is known about the regulation of corn ADH and the specific promoter regulating corn ADH expression. Insertion of stomach ADH in maize should not inactivate the endogenous corn ADH and any adverse effects on corn development are minimal and do not affect the development of the corn plant.

The ADH/ALDH composition of the invention is packaged in such a manner as to retain its biological activity in the stomach to facilitate the metabolism of ingested alcohol, preferably in a form suitable for oral ingestion immediately before drinking an alcoholic beverage. As the stomach levels of ADH are increased, more of the ingested alcohol will be metabolized in the stomach before being absorbed into the blood. This results in reduced blood alcohol levels and curtailed adverse mental and physical effects of alcohol in individuals engaged in social or business related drinking. The stomach contains a variety of proteases which may degrade ADH and ALDH. Stomach pH is variable from low levels (acidic) up to pH values in the neutral or basic range (pH=8.5). The transgenic corn kernels expressing stomach ADH and ALDH are prepared in paste, powder, pill or other form as described below, and if necessary, buffered with sodium bicarbonate or any other appropriate buffer to maintain enzymatic activity within the human stomach environment, as is well known in the art.

In the case of corn, the corn kernel may be used to produce a food or pill to be consumed before drinking alcohol to allow more alcohol to be oxidized in the stomach. Corn kernels may be homogenized and prepared as a corn paste or powder or other form to be administered as described below. The paste may be sandwiched between either cookies or crackers to facilitate its consumption. Alternatively, the paste may be dried to a powder and packaged as a pill to be ingested. In either case, an appropriate amount of the required co-factor, nicotinamide adenine dinucleotide (NAD), is added to either the paste, powder or other form. NAD is relatively inexpensive and may be purchased from a variety of sources such as American Research Products of Solon, Ohio or Schweizer Hall, Inc. of Piscataway, N.J.

As more stomach ADH is available then more ethanol will be converted to acetaldehyde. Normally, the stomach contains ALDH which converts acetaldehyde into acetic acid. To avoid the adverse effects of acetaldehyde accumulation, it is contemplated that the plant derived pills, paste or dried fruit containing ADH/NAD/bicarbonate be supplemented with stomach ALDH/NAD to ensure that the acetaldehyde concentration in the stomach does not increase.

To further protect proteins from the stomach proteases as well as the low pH of the stomach, the ADH/ALDH/NAD/bicarbonate of the invention may be packaged in a swollen gel, as disclosed in Lehr, Bioadhesion Technologies for Delivery of Peptide and Protein Drugs to the Gastrointestinal Tract, Critical Review in Therapeutic Drug Carrier Systems, Vol. II pp. 119–160 (1994). Alternatively, the ADH/ALDH/NAD bicarbonate compound may be encapsulated as a liposome pill, incorporated into hydrated lipidic lamellar phases, liposomes, or in liposome-type vesicles, the whole being incorporated or encapsulated into a pharmaceutically acceptable excipient, vehicle or carrier by known preparative techniques described for example in Kulkarni et al., *J. of Microencapsulation* 12:229–246 (1995). Alternatively, microencapsulation of drugs offers the advantage of the ability to deliver small amounts of drug at a constant or at least a controlled manner, at sites of absorption, to achieve the desired activity with a minimal amount of drug. Microencapsulation may protect the drug against harmful environmental influences such as degrading enzymes or bile salts in the gastrointestinal tract after oral administration, until the drug is actually released. Graves et al., Encapsulation Techniques, Encyclopedia of Food Science and Technology, Vol. 2, John Wiley & Sons, Inc., New York, 1992, pp. 697–703. Coating liposomes with a derivatized polysaccharide such as o-palmitoylpullulan (OPP) increases the potential of using liposomes as a drug delivery system after oral administration. Sehgal, et al., *J. Microencapsulation Vol.* 12, No. 1, 37–47 (1995).

In any case, the ethanol will be readily absorbed into the gel or pill and serve as a substrate for the ADH and ALDH. The packaged ADH and/or ALDH is dissolved in the stomach causing rapid inactivation of the enzymes within the first few hours after consumption or administration. Thus, it is preferred that the enzyme composition be taken immediately before the ingestion of alcoholic beverages. Excess ingested or administered ADH and ALDH is not harmful. Any excess ADH and ALDH will be digested or otherwise degraded in the stomach within a short time.

Definitions

The terms plant, selectable marker genes and reporter genes, transcription termination sequences, transformation and operably linked have the following meanings in this application and claims:

As used here, the term "plant" includes plant cells in planta and plant cells and plant protoplasts in culture, plant cell tissue cultures from which corn or other plants may be regenerated, aggregations of plant cells such as is present as a disorganized mass in a callus, plant clumps, and plant cells that are intact in plants or parts of plants, such as embryos, pollen, flowers, kernels, ears, cobs, leaves, shoots, seeds, fruit, husks, stalks, roots, root tips, anthers, silk and the like.

By "selectable marker genes and reporter genes" is meant a DNA sequence coding for a phenotypical trait by means of which transformed cells may be selected from untransformed cells.

By "transcription termination sequences" is meant any nucleic acid sequence which determines the position of the 3' end of a transcript. Transcription termination sequences include polyadenylation sites. By "transformation" is meant the act of causing a cell to contain a DNA sequence which did not originate in that cell. By "operably linked" is meant the chemical fusion of two fragments of DNA in a proper orientation and reading frame to be transcribed into functional RNA.

The preferred type of corn species is obtained from the American Type Culture Collection (ATCC), Rockville, Md. 20852 U.S.A. For example, a tissue culture of regenerable cells of a plant of inbred corn line (for example, public inbred lines H99, Pa91) that is highly regenerable from calli, as described in Hodges et al., *Bio./Technol.* 4:219–223 (1986), is preferred.

Applications

As contemplated herein, it is not necessary to isolate, extract or purify ADH and ALDH from the corn plant in an additional, separate process; the wet-milling process which is typically used to extract corn starch and corn gluten may be used to extract ADH and ALDH from corn. The resulting ADH and ALDH may be used in the production of pills, capsules or a food product to be eaten before ingesting alcohol. This has the advantage of utilizing corn for both its corn starch and its transgenic ADH and ALDH. Corn is the preferred plant as it has the advantages of low raw material cost (in the range of $2.00 to $2.50 per bushel or 56 pounds of dry kernels) and an existing wet milling extraction process.

In addition to its use as a dietary supplement, the resultant ADH and ALDH may also be used in higher doses in such applications as pharmaceutical and therapeutic procedures.

There are several advantages to using transgenic plants as bioreactors over bacteria or transgenic or isogenic cattle. While the estimated cost of generating transgenic plants may be high initially, the yield and overall cost of the resultant ADH and ALDH will be very low. ADH and ALDH may be extracted from transgenic corn plants using existing wet-milling technology. In contrast, ADH and ALDH produced in milk of transgenic or isogenic cattle requires extraction of the ADH and ALDH from the milk. This extraction process is an additional, separate step which is not part of milk processing as currently practiced. In practice, bacteria bioreactors can be very expensive methods to produce foreign proteins.

The use of transgenic plants has other applications as well. With appropriate gene constructs the expression of the inserted genes in transgenic plants may be controlled in a tissue-specific and in a differentiation-specific manner.

Examples of suitable monocotyledonous plants into which the gene construct may be inserted include corn (*Zea mays* Linnaeus), rice, wheat, barley, oats, millet, sorghum amaranth, onion, asparagus and sugar cane. Suitable dicotyledonous plants include alfalfa, soybean, cotton, clover, sugarbeet, sunflower, carrot, celery, cabbage, cabbage, broccoli, brussel sprouts, radish, rapeseed, cucumber pepper, canola, bean, lettuce, cauliflower, spinach, artichoke, pea, okra, squash, kale, collard greens, potato, tobacco, tomato, tea and coffee and the like.

It should be understood that the present invention is not limited to the plants described herein and other plants may be similarly employed.

Gene constructs

The invention also contemplates a gene construct which comprises a DNA sequence coding for mammalian ADH operably linked to an upstream (5') promoter sequence capable of initiating and directing transcription in plant cells of said DNA sequence. The gene construct is integrated into the plant genome such that upon transformation the plant cells express mammalian ADH. Transgenic plants are regenerated from the plant cells which have been transformed and grown for a time and under conditions sufficient to permit expression of mammalian ADH. The invention further contemplates a similar gene construct comprising a DNA sequence coding for mammalian ALDH.

The invention is also directed to seeds obtained by growing the transgenic ADH and ALDH-producing plants, ADH and ALDH produced from plants, and pills or food products which include ADH and ALDH produced from plants.

The proper regulatory signals must be present in the proper location with respect to the gene for the newly inserted ADH gene to express the protein for which it codes in the plant cell. The same is true for the newly inserted ALDH gene. These regulatory signals include a promoter sequence that directs the cellular machinery to produce RNA and a polyadenylation sequence which is a non-translated region that terminates transcription in plant cells and causes the addition of polyadenylate nucleotides to the 3' end of the RNA to stabilize the RNA in the cytoplasm for subsequent translation of the RNA to produce protein.

The promoter may be any constitutive, inducible, tissue or organ specific, or developmental stage specific promoter which can be expressed in the plant cell of choice. Constitutive promoters, such as the 35S promoter of cauliflower mosaic virus, which direct RNA production in many or all tissues of a plant and during most stages of development when integrated into the genome of transgenic plants are preferred. The 35S promoter from the cauliflower mosaic virus (CaMV35S) has been shown to be the strongest constitutive promoter known in plants and confers expression in both dicots and monocots. Odell et al., *Nature*, 313:810–812 (1985); Jensen et al., *Nature*, 321:669–674 (1986); Jefferson et al., *EMBO J.*, 6:3901–3907(1987); Kay et al., *Science*, 236:1299–1302 (1987); Sanders, et al., *Nucleic Acids Research*, 4:1543–1558 (1987). Consequently, the 35S promoter is preferred. In particular, a chimeric promoter with doubled CaMV enhancer elements, referred to herein as a CaMV35S doubled enhancer promoter, is preferred.

It is critical that the gene construct consisting of at least a promoter and the DNA sequence coding for the ADH gene (or the ALDH gene) integrates into the genome of the corn so that it is stably inherited by progeny of the transgenic corn. Stable transformation comprises the chromosomal integration, including incorporation into plastid chromosomes, of the introduced DNA so that the integrated gene sequences are passed on to progeny of the transformed plant. Stably transformed cells must also be capable of regenerating fertile, transgenic plants. Transient transformation, in contrast, does not generate transgenic plants as the introduced DNA is eventually lost. Transformed corn cells will be selected that are stably transformed and capable of regenerating fertile transgenic plants.

CLONING ALDH

Using the same strategy described above for cloning ADH, ALDH and preferably ALDH2 is cloned in plants, preferably in corn or tomatos. A similar gene construct is used with the exception that a DNA sequence coding for ALDH rather than ADH is used. Transgenic corn expressing ALDH is converted into either a powder, paste, pill or dried fruit or vegetable in combination with transgenic ADH and is supplemented with bicarbonate to buffer the acidity of the stomach, if necessary. The required co-factor NAD is added to the pill or the paste. The pill or paste contains either ALDH in combination with NAD or both ADH and ALDH in combination with NAD. Suitable buffers are added as needed. The consumer, particularly a sufferer of facial flush after alcohol consumption, may take the pill or paste immediately before drinking alcohol. The consumed alcohol will be metabolized by both the ADH and ALDH enzymes and converted into acetic acid in the stomach. Depending on the amounts consumed, some of the alcohol will be metabolized in the stomach and some will be absorbed into the blood. Any alcohol absorbed into the blood will be converted to acetaldehyde by ADH in the liver. But, as the amount of alcohol consumed increases, the effects of the consumed ADH and ALDH decreases. Individuals who normally experience facial flush are now able to consume small amounts of alcohol without many of the negative consequences of facial flush, etc.

Electroporation is the presently preferred method of introducing foreign DNA into corn. Fromm et al, *Nature*, 319:791–793 (1986); Jones et al., *Plant Mol. Biol.*, 13,501

(1989); Yang et al., *Plant Cell Reports,* 7,421 (1988); D'Halluin et al., *The Plant Cell* 4:1495–1505 (1992) and Krzyzek et al. U.S. Pat. No. 5,384,253.

Thus, the invention contemplates cloning the appropriate mammalian and preferably human ADH and ALDH genes from genomic DNA or from messenger RNA as cDNA. A cDNA construct will not contain all the introns while the genomic DNA will. Preferably, human Class IV ADH and human ALDH2 are cloned. Appropriate DNA sequences containing the ADH and ALDH gene linked to a plant specific promoter such as the CaMV35S promoter are constructed and used to transform plants, preferably, corn (maize) or tomatoes. Constructs are made using specific restriction enzymes which recognize certain sequences of bases on the DNA strand and cut where those sequences appear. Ligases are enzymes which rejoin DNA segments. The cut DNA is ligated (joined) to a DNA vector which allows the gene of interest to become incorporated into the plant genome. The vector may contain viral and/or plasmid features. Heterozygous transgenic plants that synthesize ADH are generated. Transformation occurs when the gene carried by the vector is incorporated into the DNA of the plant where it initiates production of the desired ADH. Using backcrossing techniques well known to those of ordinary skill in the art, homozygous maize for commercial planting is then generated. Transformed plants are grown and either pollinated with the same transformed strain or different strains. The resulting progeny expressing ADH are then identified. Two or more generations may be grown to insure that ADH is stably maintained and inherited and then seeds are harvested for use to provide plants expressing the desired ADH. Similar procedures are followed to obtain ALDH of mammalian and preferably of human origin.

Cloning The ADH Genes Overview

The entire complement of genes in an organism that encodes proteins needed for development and life is called the genome. In mammals, the genes are organized on chromosomes with each chromosome being a single long molecule of double stranded DNA. The DNA in the chromosomes functions as a blueprint for proteins. Many genes are encoded as a single uninterrupted sequence of nucleotides. Some genes are arranged in segments with coding regions (exons) interrupted by non-coding regions (introns). When a particular protein is needed, the code to synthesize the protein is transferred from the DNA into a molecule of messenger RNA (mRNA) by a process called transcription. The 5' end of the mRNA encodes the protein's amino terminus (beginning with the first exon) and the 3' end encodes the carboxyl terminus. Nucleotides preceding the first exon are referred to as being "upstream" from the gene and nucleotides after the last exon are "downstream" from the gene. RNA transcription is initiated at a specific upstream DNA sequence called a promoter. Transcription rate may be accelerated by the presence of sequences in the DNA called enhancer elements and these may be upstream or downstream of the promoter. After transcription, the mRNA may be further processed by splicing before leaving the nucleus. The completed mRNA enters the cytoplasm where it encounters ribosomes which translate the codes contained in the mRNA into the appropriate protein.

Where not specified, recombinant DNA procedures follow the methods of Sambrook. J., Fritsch. E. F., and Maniatis, T., *Molecular Cloning, A Laboratory Manual* Second Ed., Cold Spring Harbor Laboratory Press, Cold Spring Harbor, N.Y. (1989), incorporated herein by reference. Restriction enzymes and T4 ligase are obtained from commercial sources, such as New England Biolabs of Beverly, Mass., and used according to the manufacturer's recommendations.

Cloning the human class IV ADH gene

The gene encoding human Class IV ADH has been cloned as disclosed by Satre et al., *J. Biol. Chem.* 269(22) :15606–15612 (1994); Farrés et al., *Eur. J. Biochem.* 224, 549–557 (1994); Yokoyama et al., *Biochem. Biophys. Res. Commun.* 203(1):219–224 (1994); Yokoyama et al., FEBS Letters 351:411–415 (1994); Kedishvili et al., *J. Biol. Chem.* 270(8):3625–3630 (1995), incorporated herein by reference. In addition to the upstream promoter, stomach ADH may also be regulated by sequences within the first several introns.

Cloning the genomic ADH gene

A procedure similar to that for cloning human ADH is used for cloning mammalian, such as bovine, ADH. Specifically, a bovine genomic library is created by isolating DNA from bovine stomachs, cutting it with appropriate restriction enzymes to generate large fragments of DNA and cloning them into a cosmid vector, using standard techniques such as disclosed in Sambrook and Maniatis, *Molecular Cloning*, Second Ed., Cold Spring Harbor Laboratory Press, Cold Spring Harbor. N.Y. (1989). Large segments of DNA (30–42 kilobases) are cloned into a single cosmid. The resulting library is screened with cDNA probes made by restriction digestion of the human stomach ADH cDNA clone in the conventional way disclosed by Tromp et al., *Biochemical Journal* 253:919–922 (1988), incorporated herein by reference, to identify and isolate the bovine ADH gene. The cDNA is preferred for screening instead of the genomic human clone because the cDNA contains only exons. The cDNA probes allow detection of the exons within the bovine genomic fragments contained in the bovine genomic library. The library is screened with a probe which encodes the 5' region of the human ADH gene and subsequently positive clones are then screened with human probes encoding the far 3' region of the ADH gene. The double screening may result in a single clone containing the entire bovine ADH gene. If a full length clone is not contained within a single cosmid, the library may be rescreened with the 3' probe and positive clones analyzed for sequences which overlap the clones "pulled" from the library with the 5' probe. Restriction enzyme analysis of each resulting clone enables creation of a hybrid clone encoding the entire gene by splicing into the overlapping intron regions. Furthermore, clones which hybridize with the 5' probe but not the 3' probe may be used to identify the bovine ADH promoter and enhancer elements. These techniques result in (a) a full length genomic clone encoding the bovine ADH gene and (b) a clone containing the ADH transcriptional promoter and enhancer elements. These recombinant constructs are then used to create clones to be used for gene constructs to generate transgenic corn.

Cloning the human ALDH2 Gene

The gene encoding human ALDH2 has been cloned as disclosed by Hsu et al., *Genomics,* 2:57–65 (1988); Hsu et al., *Genomics,* 5:857 865 (1989); Hsu et al., *J. Biol. Chem.* 267:3030–3037 (1992), Hsu et al., *Proc. Natl. Acad. Sci. USA,* 82:3771 (1985), incorporated herein by reference.

The same strategy is followed to clone the bovine ALDH gene. The cloned human ALDH DNA is used in the conventional manner disclosed by Kuivaniemi, et. al., *Biochemical Journal* 525:633–640 (1988), incorporated herein by reference, to create 5' and 3' probes for the isolation of a bovine or other mammalian ALDH full length genomic clone and regulatory elements.

Cloning the Gene Encoding Bovine ADH and ALDH cDNA libraries are created from mRNA transcripts and do not contain the intronic sequences of the genomic gene. Many genomic genes are silent in differentiated or specialized cells. The active genes are transcribed and proteins synthesized from the messages. Therefore, tissue specific or differentiation specific clones can be generated from the mRNAs being synthesized at the time of RNA extraction. RNA is extracted from specialized bovine cells which synthesize ADH and double strand cDNA is synthesized using standard techniques to create a DNA bovine library encoding for bovine ADH. Total RNA is isolated from human or bovine stomachs using standard techniques, as described in Maniatis. Messenger RNA is isolated from the total RNA preparations using oligodT column chromatography, as described in Maniatis. First strand cDNA synthesis is initiated using a NotI-oligodT primer adaptor commercially available from Gibco (Long Island, N.Y.). Following degradation of the RNA template with Rnase H, the second strand of cDNA is synthesized with DNA polymerase cocktail (Gibco, Long Island, N.Y.). The double stranded cDNA molecules are treated with T4 DNA polymerase to remove single stranded overhangs and render the molecule blunt ended. The blunt ended construct is ligated to adaptors containing SalI restriction sites and cut with NotI to produce molecules with NotI/SalI sticky ends. These molecules are then ligated into pSV-SPORT (Gibco, Long Island, N.Y.) vector at the NotI/SalI cloning sites. The library is then transformed into E. coli and plated in pools of 10,000 colonies each. The library is screened with the human ADH cDNA probe as discussed above with respect to a genomic library. Positive clones are sequenced to determine whether they are full length.

The ALDH gene is isolated in a similar manner using the human ALDH cDNA as a probe as discussed above with respect to a genomic library to screen the cDNA bovine ALDH library. In all other respects, the process for ALDH is the same as for ADH.

Cloning any ADH or ALDH gene

Similar processes, as outlined above, may be followed for cloning any other ADH and ALDH gene such as ADH classes I through VI and ALDH1 through ALDH8, of mammalian and preferably human origin. The resulting clones are used for DNA constructs to generate transgenic plants. It is understood that new probes for use in cloning ADH or ALDH and new methods of cloning different types of ADH and ALDH may be developed for use in the invention.

Creation of clones for generating transgenic plants

Recombinant ADH gene constructs are used to generate transgenic plants which are able to produce ADH in their cells. Similar gene constructs are used to generate transgenic plants producing ALDH in their cells. Cloning follows established molecular biology techniques, following Sambrook, J., Fritsch, E. F., and Maniatis, T., *Molecular Cloning, A Laboratory Manual*, Second Ed., Cold Spring Harbor Laboratory Press, Cold Spring Harbor, N.Y. (1989).

Specific Examples of Gene Constructs

Four different types of gene constructs shown in FIGS. 1–4 and described below are preferred. The preferred gene constructs are integrative (integrate into host DNA). Two specially designed vectors (pZM1 and pZMA2) are used as the final gene constructs to insert either the cDNA or genomic clone of the ADH or the ALDH genes. The construction of these vectors proceeds as follows:

The CaMV5S promoter used herein is described in Benfey and Chua, *Science* 250:959–966 (1990). Analysis of the CaMV35S promoter indicates two domains, domain A from nucleotide −90 to +8, and domain B from nucleotide −343 to −90, as well as five subdomains, B 1 through B5, whose end points are indicated below, located upstream of the Tata region (−46 to +8) of the CaMV35S promoter.

| B5 | B4 | B3 | B2 | B1 | A1 | TaTa |
|---|---|---|---|---|---|---|
| −343 | −301 | −208 | −155 | −105 | −90 | −46 +8 |

Octopine Ti plasmids carry an ocs gene which encodes octopine synthase (lysopine dehydrogenase). Koncz et al., *EMBO J.* 2:1597–1603 (1983) provides a functional analysis of ocs. Nopaline Ti plasmids encode the nopaline synthase gene (nos) (sequenced by Depicker et al., *J Mol. App. Gen.* 1:561–573 (1982)). A functional analysis of nos is provided by Shaw et al., Nucl. Acids Res. 12:7831–7846 (1984).

Plasmid pKM794, which uses plasmid pUC 19 as the prokaryotic backbone, is described in Omirulleh et al., *Plant Molecular Biology*, 21:415–428 (1993) as attributed to Drs. E. Fejes and F. Nagy (unpublished). Referring to FIG. 5, plasmid pKM794 contains a chimeric CaMV double enhancer promoter sequence which is comprised of a tandem repeat of domains B3-A 1 (nucleotides −208 to −46) located upstream of the promoter domains A1 and TaTa (nucleotides −90 to +8). This chimeric promoter directs the transcription of a reporter gene encoding a bacterial Beta-glucuronidase (GUS) gene. The NOS transcription termination sequence downstream from the GUS coding sequence is fused to the 3' end of the GUS gene. The chimeric CaMV enhancer/promoter has been shown to increase GUS reporter gene expression in corn more than 10 fold over that produced with the native CaMV promoter alone. Omirullah, *Plant Molecular Biology*, 21:415–428 (1993).

The 260 base pair fragment containing the chimeric doubled enhancer CaMV35S promoter element is excised by digestion with Hind III and Bam HI and separated from the rest of the plasmid by agarose gel electrophoresis, as shown in FIG. 5. The fragment is excised from the gel and purified by phenol extraction and ethanol precipitation.

Figure 6:
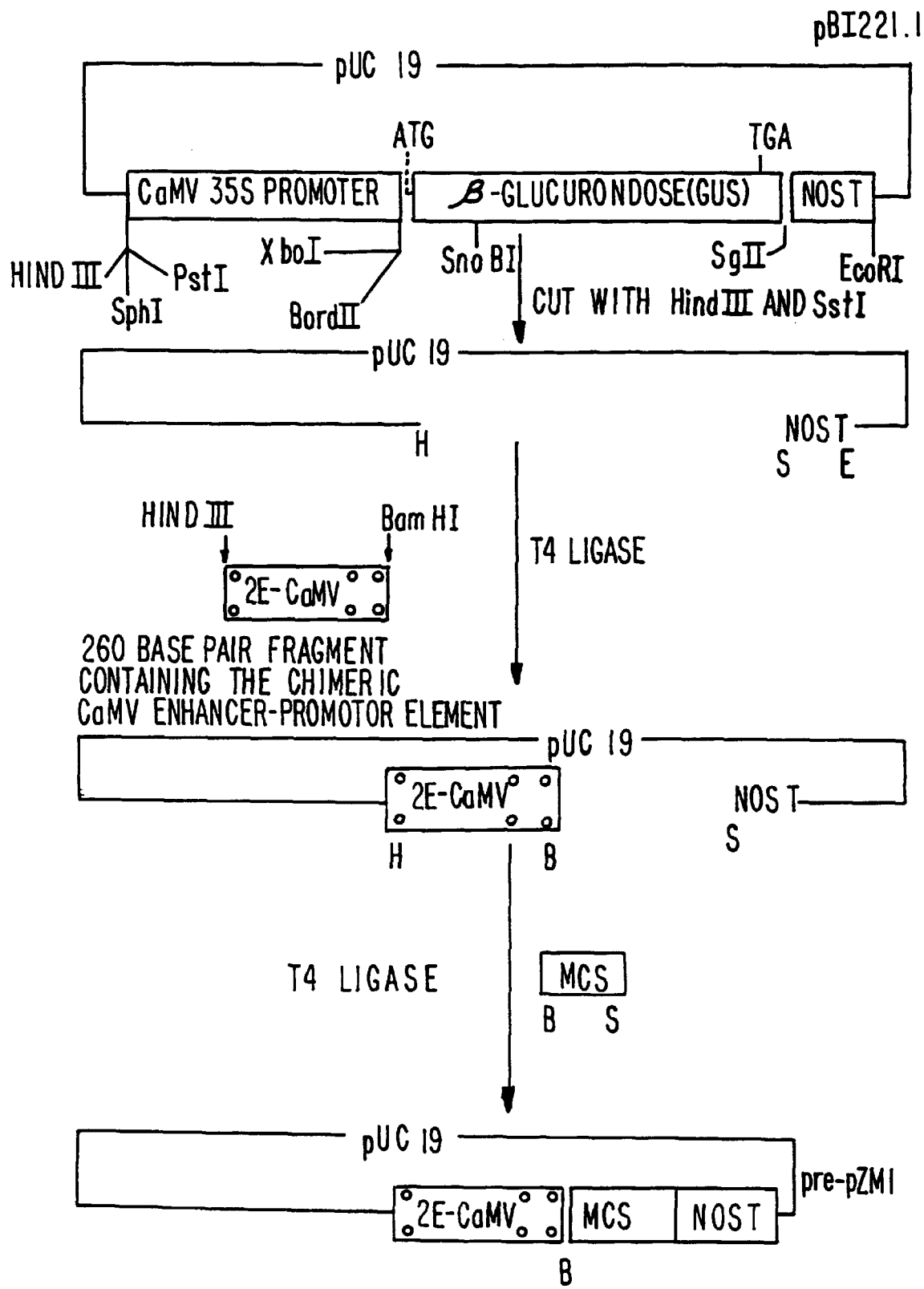
FIG. 6 is a map showing the formation of of plasmid pre-pZM1.

Referring to FIG. 6, plasmid pBI221.1 is a derivative of plasmid pBI121.1 described in Jefferson et al. *EMBO Journal* 6:3901–3907 (1987) and Jefferson et al., Genetic Engineering, Vol. 10 pp. 247–263 (1988). Plasmid pBI221.1 is a vector in which the 3.0 kb HindIII-EcoRI fragment of pBI121.1 containing the CaMV35S promoter fused to the B-glucuronidase (GUS) gene and terminating with the nopaline synthase gene termination and polyadenylation sequences (NOS-ter) has been cloned into the corresponding sites of pUC19 to facilitate high-yields of plasmid DNA from bacterial hosts. The CaMV35S promoter and the GUS gene are excised with HindIII and SstI. The fragments are separated by agarose gel electrophoresis and purified as described above.

The fragment comprising the pUC19 and NOS terminator (NOST) of plasmid pBI221.1 is excised with HindIII and SstI and gel purified as described above. The isolated fragment is then ligated to the chimeric promoter fragment from pKM794. Thus, the chimeric promoter is substituted for the native CaMV promoter.

A multiple cloning site polylinker containing 5' BamHI sticky ends, unique internal restriction sites for XbaI, SmaI, SalI, NcoI, HindIII, XhoI, KpnI, NotI, and 3' SstI sticky ends is synthesized commercially and ligated to the above construct downstream of the double enhancer promoter to allow easy insertion of the ADH or ALDH gene or other elements. This construct is referred to as pre-pZM 1.

Figure 7:
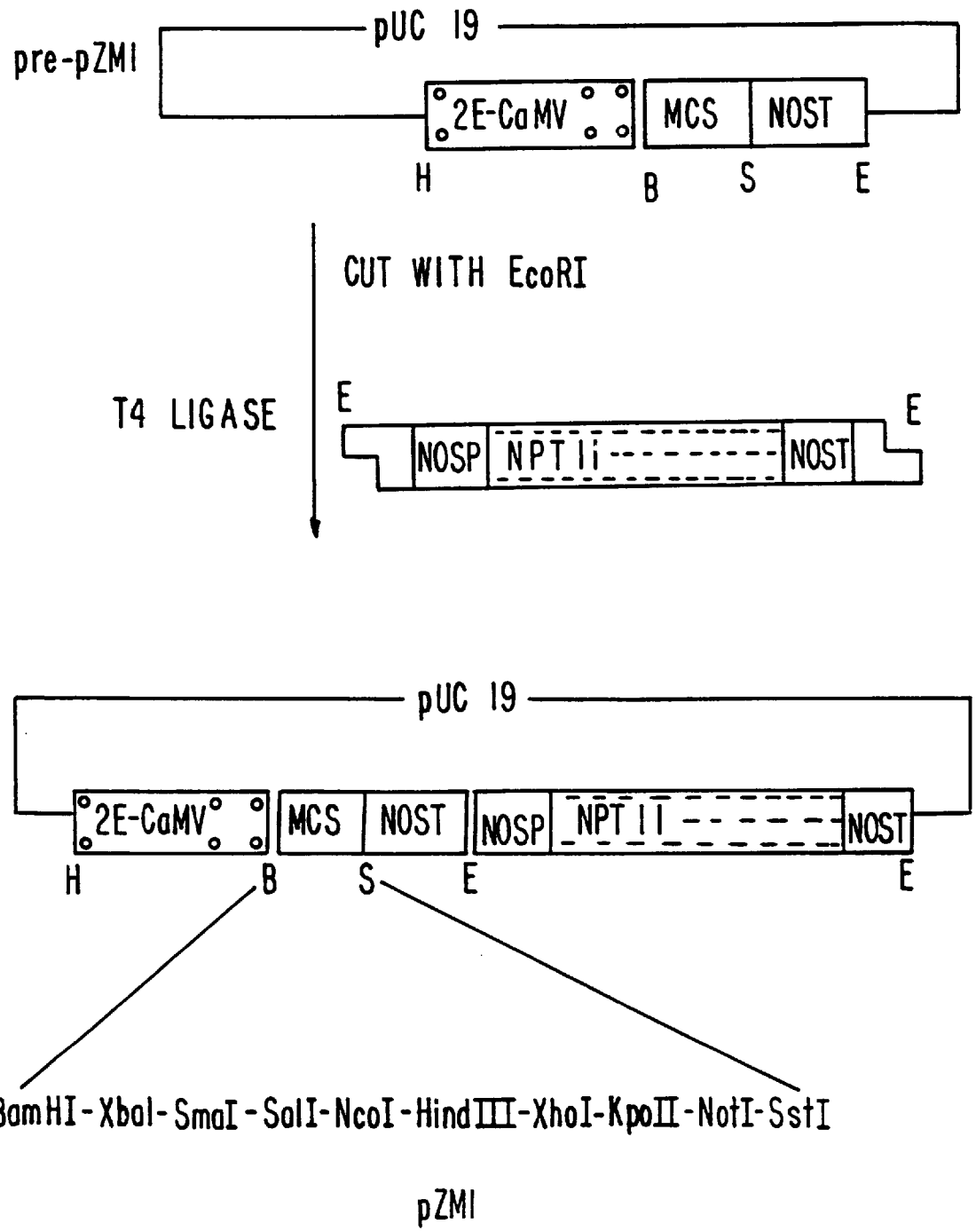
FIG. 7 is a map showing the formation from plasmid pre-pZM1 to plasmid pZM1.

Plasmid pUC9-nopneoΔ is described in Bevan et al., *Nuc. Acids Res.* 12(22):8711–8721 (1984). Referring to FIG. 7, this vector contains the neomycin phosphotransferase II (NPTII) gene under the direction of the nopaline synthase promoter (NOSP). NPTII encodes a protein which inactivates neomycin and kanamycin making organisms expressing this gene resistant to both drugs. The nopaline synthase terminator and polyadenylation sites (NOST) are downstream (3') of the NPTII gene. This transcription unit is cloned into the HindIII/EcoRI sites of the pUC9 prokaryotic vector. The vector is digested with HindIII and EcoRI and the entire transcription unit comprised of NOSP fused to NPTII fused to NOST is isolated by agarose gel electrophoresis. The ends are filled in with T4 DNA polymerase and EcoRI sticky end adaptors are ligated with T4 ligase. This removes the HindIII site and allows the NPTII transcription unit to be cloned into the EcoRI site of plasmid Pre-pZM1. As shown in FIG. 7, this new construct is called pZM1 (plasmid Zea mays 1) and is the basic vector into which the ADH or ALDH genes are inserted. Plasmid pZM1 is a novel vector and may be used to insert any gene of interest such as insulin.

The vector pZM1 is carried by the pUC19 prokaryotic backbone. It contains the neomycin/kanamycin resistance gene (NPTII) as a eukaryotic selectable marker under the transcriptional regulatory signals of the nopaline synthase promoter and terminator. This vector contains multiple cloning sites (MCS) located between the CaMV double enhancer promoter and the nopaline synthase terminator (NOST).

Other elements such as leader sequences, introns, enhancers, polyadenylation sequences and the like may optionally be included in the foreign DNA to improve expression or functioning of the introduced DNA in the plant by affecting transcription, stability of the mRNA, etc. For example, insertion of the maize alcohol dehydrogenase 1 intron 1 (Adh-1) (Callis et al., *Genes and Develop.* 1,1183–1200 (1987)) or the 5'region of the rice actin 1 intron 1 (Act-1) sequences (McElroy et al., *Mol. Gen. Genet.* 231:150–160 (1991)), between a promoter and a coding sequence in a particular recombinant DNA construct leads to a 10–65 fold increase in production of a reporter enzyme in transgenic maize plants. (Callis et al., supra). However, even without inclusion of an intron or enhancer element in the gene construct, sufficient expression for a selectable marker to facilitate identification and selection of transformed cells may) often be obtained. Klein et al., *Plant Physiol.,* 91, 440–444 (1989). Gene constructs containing the Act-1 enhancer elements contained within the introns are preferred to increase expression of the ADH gene in maize cells. Referring to FIG. 3, the the 5' region of the rice actin I intron is inserted 3' to the CaMV35S doubled enhancer promoter. The Act 1 intron 1 gene is obtained by digestion of plasmid pBCG-A4 with XbaI and NcoI as disclosed in McElroy et al., *Mol. Gen. Genet.* 231:150–160 (1991) and is inserted into pZM1 at the ZbaI/NcoI sites. Referring to FIG. 4 the gene construct is identical to FIG. 3 except that the gene for ALDH is used rather than the gene for ADH.

Figure 8:
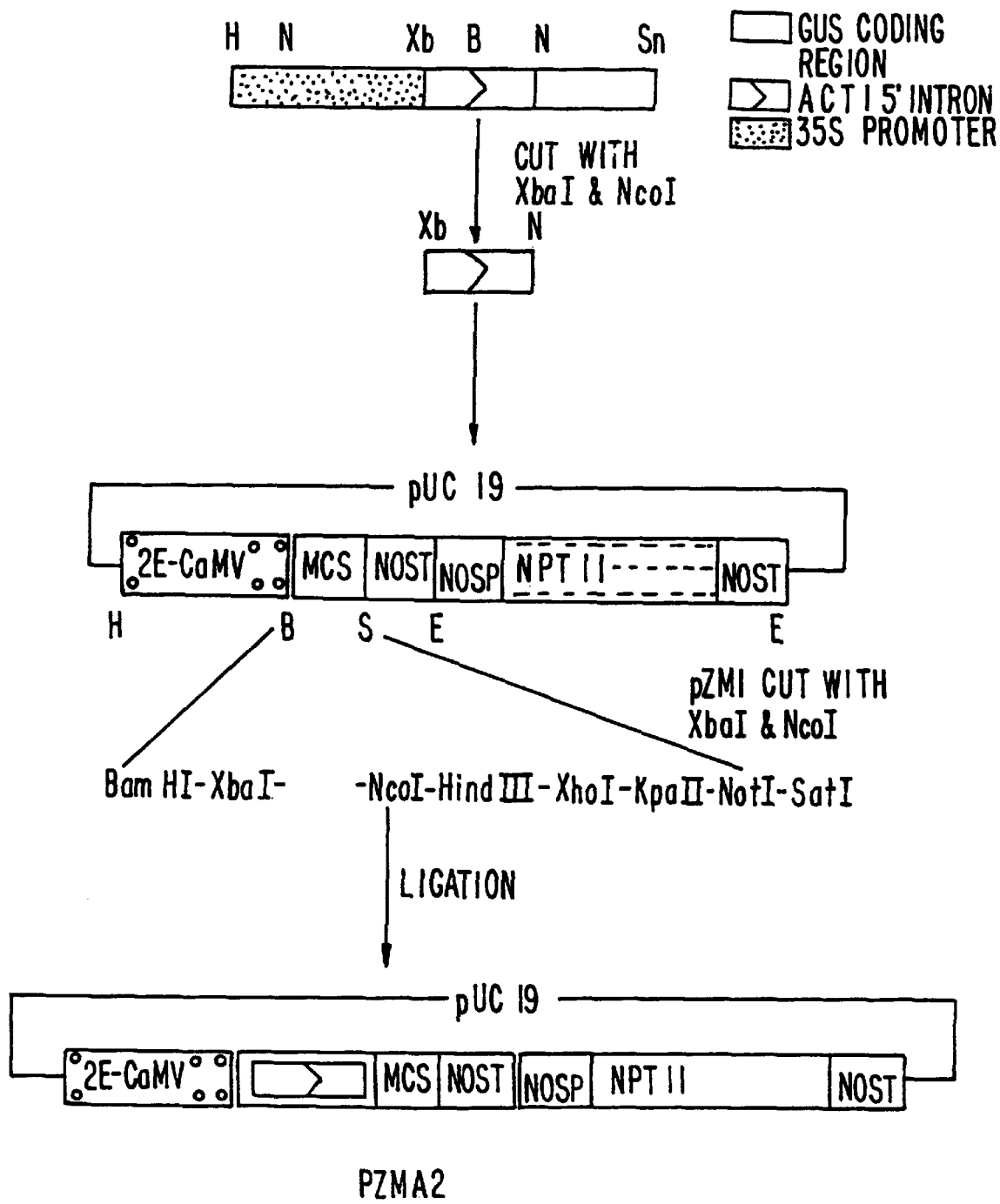
FIG. 8 is a map showing the formation from plasmid pZM1 to pZMA2.

Referring to FIG. 8, plasmid pBCG-A4 described by McElroy et al., *Mol. Gen. Genet.* 231:150–160 (1991), uses a native CaMV35S promoter and a 5' region of the rice actin 1 intron 1 to direct RNA transcription of the GUS reporter gene in Zea mays. The prokaryotic backbone of this vector is pBluescriptII-ks (Stratagene, La Jolla, Calif.) and it was designed to have the Kozak consensus sequences around the NcoI restriction site. The 316 base pair XbaI/NcoI fragment of the rice actin 1 intron I (Act-1) is isolated by agarose gel electrophoresis as described previously. This fragment is ligated into the vector construct pZM1 within the multiple cloning site at the XbaI/NcoI sites. The new vector containing the doubled enhancer CaMV35S promoter and the Act-1 5' intron is called pZMA2 (plasmid *Zea mays* 2). The ADH and ALDH genes are subcloned into pZMA2 as shown in FIGS. 3 and 4, respectively. Plasmid pZMA2 is a novel vector and may be used to insert any gene of interest, such as insulin.

Constructs using the cDNA human or animal clone

The cloned human or animal cDNA prepared as described above is put under the regulatory control of the cauliflower mosaic virus 35S promoter utilizing conventional genetic manipulation techniques.

Constructs using the cDNA bovine clone

The cloned bovine cDNA prepared as described above is put under the regulatory control of the cauliflower mosaic virus 35S promoter utilizing conventional genetic manipulation techniques.

Generating transformed plant cells

The preferred gene constructs for producing ADH and the preferred gene constructs for producing ALDH are as follows:

Referring to FIGS. 1 and 2, the preferred gene construct is pZM1 which may be the cloned human class IV ADH or the cloned bovine class IV ADH or any member of the ADH gene family as defined above 5' to the start codon for protein translation. The ADH genomic DNA is cloned into the multiple cloning site in the vector backbone at the designated sites using SAlI endonuclease. For ADH cDNA insertion, the insert is cut with NotI and SalI and ligated into the NotI/SalI sites of pZM 1. If the pZMA2 vector is used, then the ADH cDNA insertion is cut with NotI/SalI made blunt ended with T4 DNA polymerase and having HindIII adaptors ligated to it. The ADH cDNA is then cloned into the HindIII site of the multiple cloning site of the vector pZMA2. The gene construct is then introduced into a plant for integration into the host chromosome as discussed below.

Referring to FIG. 2, a similar gene construct is used for producing ALDH with the exception that the promoter is fused to the ALDH gene, which may be the cloned human ALDH2 or the cloned bovine ALDH, or any member of the ALDH gene family. For the ALDH cDNA, the clone is cut with NotI/SalI, made blunt ended with T4 DNA polymerase and ligated into the NotI/SalI sites in vector pZM1. If the pZMA2 vector is used, then the ALDH cDNA insertion is cut with NotI and SalI made blunt ended with T4 DNA polymerase and having HindIII adaptors ligated to it. The ALDH cDNA is then cloned into the HindIII site of the multiple cloning site of the designed vector pZMA2.

Constructs using the cDNA bovine clone

A transcription termination sequence including a polyadenylation signal is fused to the 3' end of the CaMV35S doubled enhancer promoter sequence—ADH gene. The transcription termination sequence may be obtained from the same source as the promoter (i.e., from CaMV) or may be obtained from a different source. Omirulleh et al., *Plant Mol. Bio.* 21:415–428 (1993) discloses a 260 base pair sequence containing a 3' transcription terminator sequence of the nopaline synthase gene in plasmid pKM794. This 260 base pair sequence is derived from restriction digest of plasmid pKM794 with SacI and EcoRI and is ligated to the 3' end of the doubled enhancer promoter sequence—ADH gene using techniques as disclosed by Maniatis. Alternatively, restriction digest of plasmid pNA2G disclosed by Omirulleh et al., *Plant Mol Bio.* 21:415–428 (1993) with EcoRI and PstI releases the CaMV35S terminator/polyadenylation fragment, which is then ligated to the 3' end of the doubled enhancer promoter sequence—ADH and ALDH gene as discussed above. Another vector construct, pDE108, disclosed in D'Halluin, *The Plant Cell* 4:1495–1505 (1992), uses an octopine synthase termination/polyadenylation nucleotide sequence which is released from pDE 108 by cleavage with NcoI and Hind III and subsequently ligated to the 3' end of the doubled enhancer promoter sequence—ADH gene.

The foreign DNA coding for ADH to be introduced into the plant preferably contains a selectable marker or a reporter gene, or both, effective in plant cells to aid in isolation of transformed cells and to promote identification and selection of transformed cells. The selectable marker may alternatively be carried on a separate piece of DNA and used in a co-transformation procedure. The selectable marker and/or reporter genes are flanked with appropriate regulatory sequences to enable expression in plants. Selectable markers useful in the invention include genes encoding resistance to an antibiotic, such as kanamycin, G418. hygromycin, streptomycin and the like. Other markers may be used in addition or alternatively, such as are well known in the art, for example, a gene coding for herbicide tolerance such as tolerance to glyphosate. sulfonylurea, phosphinothricin, or broxynil. A preferred drug resistance marker is the gene whose expression results in neomycin or kanamycin resistance. After transforming the plant cells, those cells having the gene construct will be identified by their ability to grow on a medium containing the particular antibiotic.

Reporter genes encode easily assayable marker proteins whose expression is manifested by some easily detectable property, e.g., change in phenotype or enzyme activity. Reporter genes are not present in or expressed by the recipient cell or tissue. They are used to determine whether a specific foreign DNA sequence can transform a plant cell. Preferred reporter genes include the luciferase genes from firefly *Photinus pyramis*. After the foreign DNA is introduced into the recipient cells, cells are assayed for expression of the reporter gene.

After each cloning, the construct may be isolated and subjected to further manipulation, such as restriction, insertion of new fragments, ligation, deletion, resection, insertion, in vitro mutagenesis, addition of polylinker fragments, etc. in order to provide a vector which satisfies the particular requirements. Before transformation of plant cells, the gene construct is excised from the bacterial vector with appropriate restriction enzymes and purified by agarose gel electrophoresis to remove any bacterial vector DNA. The resulting gene construct is used for transformation.

A similar procedure is followed with the exception that the ALDH gene is substituted for the ADH gene as shown in FIGS. 2 and 4.

MAMMALIAN ADH AND ALDH PRODUCTION IN YEAST AND BACTERIA

Alternatively, mammalian ADH may be expressed in yeast, preferably the methylotrophic yeast, *Pichia pastoris*, using a Pichia Expression Kit available under license from Invitrogen, San Diego, Calif. Such proteins as human serum albumin and invertase have been successfully expressed in *Pichia pastoris*. In the absence of glucose, *Pichia pastoris* metabolizes methanol as a carbon source. The Pichia Expression Kit utilizes the AOX1 promoter which controls the gene that codes for the expression of alcohol oxidase, a enzyme which catalyzes the first step in methanol metabolism. The AOX1 promoter, which is induced by methanol, is incorporated into a series of Pichia expression vectors, such as pHIL-S1 and pPIC9, which allow secretion of the recombinant product into the culture supernatant. The mammalian ADH or ALDH gene of interest is cloned into the supplied expression vector and integrates into the Pichia genome. The addition of methanol induces expression of the recombinant ADH or ALDH.

As yeast produces its own form of ADH, production of large quantities of mammalian ADH in yeast is not detrimental to the growth and development of the yeast.

Similar known methods may be employed to express mammalian ADH or ALDH in bacteria, such as *E. coli*.

Corn Tissue Culture

Unless otherwise specified, corn tissue culture procedures are as described in Green and Rhodes, "Plant Regeneration in Tissue Culture of Maize", Maize for Biological Research (Plant Molecular Biology Association, Charlottesville, Va. 1982, at 367–372) and in Duncan, et al., "The Production of Callus Capable of Plant Regeneration From Immature Embryos of Numerous *Zea Mays* Genotypes", 165 *Planta* 322–332 (1985). Methods of preparing and maintaining calli from maize tissue are described in R. Phillips et al., Corn and Corn Improvement, Agronomy Society of America (3d ed., 1988) at pages 345–387.

Transformation of maize cells

The particular manner of introducing the plant vector into the host is not critical to practice the present invention. Any method of efficient transformation may be used as is known to those skilled in the art. Methods to introduce ADH and ALDH gene into plants include the direct transfer of DNA by microinjection, electroporation, DNA entry aided by polyethylene glycol, use of plant transformation vectors derived from the tumor inducing (Ti) plasmids of *Agrobacterium tumefaciens*, chemicals that increase the free uptake of DNA, liposome fusion, use of a particle gun to inject DNA-coated microprojectiles microinjection, transformation using viruses or pollen, and the like. There are advantages and disadvantages to each of these methods. A particular method of introducing the gene construct into a particular plant species may not be the most effective for another plant species. For instance, Agrobacterium mediated transformation has been used successfully to transform dicotoleydonous plants but its utility for monocot transformation is limited. Electroporation is the presently preferred method for transformation of corn so that the foreign DNA is stably integrated in the corn plant genome and inherited by progeny of the transformed corn plants. D'Halluin et al., *The Plant Cell*. 4:1495–1505 (1992). U.S. Pat. No. 5.384,253 to Krzyzek et al, incorporated herein by reference, discloses a preferred method of transforming corn via electroporation.

Transformation of Corn Plants

To successfully produce fertile transgenic plants by electroporation, target cells are treated to render them competent for uptake of foreign DNA without significantly reducing viability. These "transformation-competent" cells incorporate the foreign DNA at appropriately high frequencies to stably transform a sufficient number of cells. The transformed cells are capable of maintaining cell division and regenerative capacity throughout the selection processes necessary to confirm and identify stably transformed cells. The transformed regenerated plants are capable of passing on the introduced DNA to progeny so that the progeny express the introduced DNA.

Three types of cells are preferred for use in transformation and subsequent production of transgenic maize: (a) immature zygotes isolated from ears, (b) type I callus produced by culture of immature zygotes, and (c) suspension cultures of type II callus generated from the type I callus cultures.

Preparation of callus and suspension cell cultures

Regenerable maize suspension cell cultures may be derived from a number of plant tissues. Preferably, the cell cultures are derived from calli generated from immature maize embryos which are removed from the kernels of an ear when the embryos are about 1–3 mm in length (about 9–14 days after pollination). Embryos are aseptically isolated and placed on nutrient agar initiation/maintenance media with the embryo root/shoot axis down (scutellum up). The initiation maintenance media (i.e., F medium, obtained from Gibco, Grand Island, N.Y.) consists of N6 basal media (Chih-ching, Proceedings of Symposium on Plant Tissue Culture, May 25–30, 1978, Science Press, Peking, pp. 43–50) with 2% (w/v) sucrose. 1.5 mg/liter 2,4-dichlorophenoxyacetic acid, 6 mM proline, 200 mg/l casein hydrolysate and 0.25% Gelrite (Kelco, Inc., San Diego). Callus tissue (type I) appears and grows from the scutellum after several days to a few weeks. The callus tissue from the scutellum is evaluated for friable consistency and the presence of well-defined somatic embryos which would indicate that the cultures are regenerable under proper conditions. Tissue is of "friable consistency" when it is easily dispersed without causing injury to the cells. Tissue meeting this definition is transferred to fresh media and subcultured on a routine basis about every two weeks.

After about 4–6 months, the established callus cultures is referred to as type II callus and is transferred to liquid growth media. Methods for producing regenerable suspension cell cultures are described by C. E. Green et al. in Maize for Biological Research, Plant Molec. Biol. Assoc. (1982) at pages 367–372; R. Phillips et al., Corn and Corn Improvement, Agronomy Soc. Amer., (3d ed., 1988) at pages 345–381; and I. Vasil, Cell Culture and Somatic Cell Genetics of Plants, Vol. I, Laboratory Procedures and Their Applications, Academic Press (1984) at pages 152–158. The liquid growth media for suspension cell cultures is typically of similar formulation to F media with ABA (abscisic acid) ($10^{-7}$M) added to augment regenerative capacity and enhance culture vitality. The callus is preferably not sieved prior to introduction into the liquid growth media. The cultures in liquid media are subcultured as appropriate to maintain active growth.

Preparation of Transformation-Competent Cells

"Transformation-competent cells", defined as cells having an increased ability to take up, express and integrate foreign DNA by electroporation as compared to untreated cells, are prepared by partially enzymatically degrading the cell walls of the cells by the controlled exposure of cells to one or more pectin-degrading enzymes. Hydrolysis of the pectin component of the cell wall is believed to increase the cell's permeability to foreign DNA while preserving the viability of the cell. In contrast, previous production of transgenic dicots has been accomplished by completely enzymatically degrading the cell walls of type II callus thereby creating a type of competent cells termed protoplasts. However, electroporation of monocot protoplasts (i.e., maize) results in extremely low transformation rates and often phenotypically abnormal plants (i.e., reduced size, seed number and viability). Krzyzek et al., supra: D'Halluin et al., The Plant Cell 4:1495–1505 (1992).

Transformation competent cells prepared as disclosed in Krzyzek et al., U.S. Pat. No. 5,384,253, are morphologically and physiologically different from protoplasts in a number of ways including the shape and conformation. Transformation-competent cells retain the out-of-round shape of callus cells and consist of stable multicell clumps in culture while protoplasts are spherical and unless they reversibly agglutinate. do not clump. As portions of the cell wall are still intact, transformation-competent cells are stainable with Tinapol BPOT (Ciba-Geigy), a cellulose-specific stain. No staining is observed with protoplasts as the cells wall is completely degraded.

Polysaccharidase enzymes such as one or more pectin degrading enzymes are used to break down part of the maize cell walls. The term "pectin degrading enzyme" includes enzymes that catalyze the breakdown of pectin and pectin subunits. Examples of pectin-degrading enzymes include endopectin lyase, pectin lyase, pectolyase, endopolygalacturonase, and polygalacturonase, as well as pectinase. Other enzymes such as xylanase, cellulase, hemicellulase, driselase, transeliminase, or macerozyme, may also be used in combination with pectin-degrading enzymes. Pectolyase (Sigma Chem. Co., St. Louis, Mo.), a combination of endopectin lyase and endopolygalacturonase, is preferably used to prepare transformation-competent cells. It is also available from Seishin Pharmaceutical Co. (Tokyo, Japan) as "Pectolyase Y-23".

Enzymatic treatment is carried out for a time sufficient to partially break down the maize cell walls without adversely affecting the viability, mitotic activity or regenerative capacity of the cells as disclosed by Krzyzek et al., supra. For a dilute solution of enzyme(s) (0.1–1%) digestion time ranges from about 0.75 to 3.0 hours, preferably from about 1.5–2.0 hours for a packed volume of about 1–2 ml of maize cells/5 ml enzyme buffer at about room temperature. Optionally, the cultured maize cells are declumped by sieving or filtering to increase the cell wall surface area exposed to enzymatic action. Following partial degradation of the cells walls, the cells are washed with buffer in an amount sufficient to substantially remove residual enzymes.

Electroporation of Suspension Cultures

The gene construct of the invention is introduced into cultures of transformation-competent maize cells prepared as described above by electroporation to obtain transformed cells which are regenerable into fertile transgenic maize plants. Potter et al., PNAS USA. 81, 7161 (1984) describes a suitable electroporation apparatus for use in the invention. Such devices typically consist of an electronic device including a capacitor. The capacitor is charged and incorporated into a circuit in series with the cells to be electroporated in an electroporation buffer. The capacitor is then discharged so deliver a current pulse to the cells. The waveform, pulse length and number of pulses delivered and pulse field conditions may be varied to optimize cell viability and levels of expression of the transformed cells.

Electroporation of transformation-competent cells is preferably performed within about 45 minutes of their preparation, although transformation-competent cells left for as long as 3 hours before electroporation may be transformed at acceptable frequencies. Electroporation is performed in an electroporation chamber in the presence of electroporation buffer at room temperature (20°–30° C.). K. J. Puite, Plant Cell Reports, 4(5):274–276 (1985). The formulation, osmolarity, pH, concentration and ionic composition and other parameters of the electroporation buffer are adjusted to optimize cell viability and transformation.

The electroporation buffer must be compatible with, and must not be toxic or otherwise adversely affect the cells to be transformed. The electoporation buffer will generally contain the gene construct, a buffering agent to maintain the pH of the electroporation buffer between about 7 and 7.7, preferably at about 7.5, and an osmoticum. Suitable buffering agents include HEPES, (N-[2-hydroxyethyl]piperazine-N'-[2-ethanesulfonic acid]) and sodium phosphate, and mixtures thereof. The osmoticum in the electroporation buffer is a compound(s) that helps maintain an osmotic balance between the extracellular medium and the interior of the transformation-competent maize cells, so cell viability is preserved. Preferred osmotica are sugars such as fructose, sucrose and the like and polyols, preferably $C_2$–$C_6$ polyols such as mannitol, sorbitol, glycerol and the like. The optimal concentration of the osmoticum is approximately 0.3–0.5M. The use of mannitol was found to lead to a consistently higher rate of transformation than using either sorbitol or sucrose.

The gene construct present in the electroporation buffer may be in supercoiled or linear form. In preferred embodiments, linear double-stranded DNA, e.g., from recombinant plasmids, is employed. Although concentrations as low as about 1 μg/ml per 1.0 ml of electroporation buffer may be used, it is preferred that the DNA gene construct be at a concentration of about 100 μg/ml or greater.

Selection of Transformants

The cells are placed on a recovery medium following electroporation and penetration of the gene construct into at least some of the transformation-competent cells. The recovery medium is preferably a solid callus maintenance medium containing mannitol. The mannitol is preferably removed after one week and recovery on maintenance media is continued for an additional week before selection begins. The extent of the recovery period varies depending on the selection agent used, and/or the number of cells electroporated. The recovery period affords cells an opportunity to recover from electroporation and permits the cells to proliferate and stabilize so that adequate numbers of cells may be generated to facilitate selection and subsequent regeneration.

Identification and selection of those cells which both contain the gene construct and which are capable of regeneration to form plants is begun between 1 day and 4 weeks, preferably at about 1.5–2.5 weeks following recovery. There are two methods for selecting the transformed cells. The first comprises assaying transformed cells within calli or plants regenerated therefrom for the expression of reporter genes or assessing the phenotypic effects of the gene construct, if any. The second, preferred method comprises identifying the transformed cells by growing the cells in the presence of an antibiotic, i.e., kanamycin, which is toxic for non-transformed cells, but allows growth of those cells transformed with and expressing the introduced gene construct including the selectable marker gene (i.e., neomycin resistance). Selection conditions are chosen to optimize growth and accumulation of the transformed cells while simultaneously inhibiting growth of the non-transformed cells. The selection agent's effect on cell viability, regeneration capacity and fertility is monitored and determined by experimentally establishing the concentration range which inhibits growth. This may be done by plotting a growth inhibition curve for the given selective agent and tissue being transformed.

A selection regimen may include sequential changes in the concentration of the agent and multiple selection cycles. Concentration and cycle length vary depending on the selection agent used. For instance transformed suspension cultures may be selected by growing the cultures in the presence of kanamycin 200 mg/L for a period of 3–6 weeks followed by selection on 60 mg/l for 3–6 weeks.

Transformation of putative transformants is confirmed by phenotypic and/or genotypic analysis. The presence of the gene construct may also be confirmed by conventional means, i.e., by Southern blot or by polymerase chain reaction (PCR). As the gene construct includes a plant expressible marker encoding the neomycin resistance gene, the plant cells are selected by culturing the plant cells in the presence of neomycin.

Plant Regeneration and Seed Production

Transformed cell lines are regenerated into transgenic whole plants in a conventional manner well known in the art and the fertility of the resultant plants is determined. Transformed cell lines which test positive by genotypic and/or phenotypic analysis are placed on a media which promotes tissue differentiation and plant regeneration. Regeneration procedures typically include reducing the level of auxin and adding sucrose which discontinues proliferation of a callus and promotes somatic embryo development or other tissue differentiation. An example of a regeneration procedure is given in C. E. Green et al., Maize for Biological Research. Plant Molec. Biol. Assoc., Charlottesville, Va., pps. 367–372 (1982). The regenerated plants may be transferred to standard soil conditions and cultivated in a conventional manner. After the gene construct is stably incorporated into regenerated transgenic plants, it can be transferred to other plants by appropriate sexual crosses and selfs as described by M. Neuffer, ibid. at pages 19–30. Any of a number of standard breeding techniques may be used depending on the species to be crossed. The plants are grown and harvested using conventional procedures.

Analysis of R1 progeny

The initial plants generated from the transformed callus are termed the R0 generation or R0 plants. The term R1 progeny or the R1 generation refers to the seeds produced by various sexual crosses of the R0 generation plants. The progeny derived from the germination of R1 seeds are also referred to as the R1 generation.

Various tissues of the R1 generation are analyzed to confirm the successful transmission and inheritance of the gene construct in the sexual crosses described above. The analysis is performed as described above for analysis of the electroporated callus for evidence of transformation except that plants and plant parts rather than callus are being analyzed.

Production of Commercial Hybrid Seed

It is advantageous to incorporate the gene construct of the invention into many varieties of hybrids which differ in maturity, yield, pest resistance, and other agronomic traits. Hybrids adapted to growth in one part of the corn belt may not be adapted to growth in other parts of the corn belt due to variations in such traits as maturity, disease, and insect resistance. It is therefore advantageous to integrate the gene construct into many parental hybrid lines to increase the hybrid combinations that may be produced containing the gene construct. This is accomplished by breeding programs in which backcrossing is performed by crossing the initial fertile. transgenic plant to an elite inbred line and then crossing the progeny back to the elite parent using conventional methods. Elite lines are pure breeding inbreds having commercially valuable traits as a result of classical breeding methods. Some of the progeny from this cross will carry the gene construct and some will not. The plants carrying the gene construct are then crossed again to the elite parent resulting in progeny which segregate once more. Repeated crosses are performed until the original elite line is converted to a genetically engineered line containing the gene construct and all other important traits present in the elite parent. A separate backcrossing program is employed for every elite line to be converted to a genetically engineered elite line. Using conventional breeding techniques, it is possible for both parents of a hybrid seed corn to be homozygous for the gene construct. Corn breeding techniques required to transfer genes from one line or variety to another are well-known.

Alternatively, the gene construct may be delivered by electroporation into immature zygotic embryos preconditioned with a mild enzymatic treatment of immature embryos or into type I callus preconditioned with cutting and preplasmolysis of type I callus. D'Halluin et al., *The Plant Cell* 4:1495–1505 (1992). The next section describes an electroporation treatment of immature zygotic embryos, followed by a description of electroporation of type I callus, following the procedure of D'Halluin et al., supra.

Electroporation, Selection and Regeneration of Immature Zygotic Embryos

Freshly excised immature embryos of H99 or Pa91 are treated for 1–3 minutes with an enzyme solution containing CPW salts (Frearson et al, *Dev. Bio.* 33, 130–137 (1973) supplemented with 10% mannitol, 5 mM Mes, pH 5.6 and 0.3% macerozyme (Kinki Yakult, Nishinomiya, Japan) or other combinations of pectin degrading enzymes. The embryos are then rinsed in appropriate buffers to remove residual enzymes. The transformation-competent cells are transferred to a microcuvette containing 200 µL maize EPM electroporation buffer (80 mM KCl, 5 mM $CaCl_2$, 10 mM Hepes and 0.425M mannitol, pH 7.2) and 10–20 µg/ml gene construct and incubated for 1 hour. The cuvettes are then incubated in an ice bath for 10 min. and then transferred to an electroporation chamber. Several pulse protocols may be tested to determine the optimal conditions. For instance, electroporation may be carried out by discharging one pulse with a field strength of 375 V/cm from a 900 µF capacitor as described by D'Halluin et al., The Plant Cell 4:14951505 (1992). The pulse strength, capacitance, and electroporation apparatus are as described by Dekeyeser et al., *Plant Cell* 2:591–602 (1990). After electroporation, the embryos are transferred to recovery media (F medium or F medium supplemented with 0.2M mannitol) or directly to selection media (F medium supplemented with 0.2M mannitol and 200 µg/ml kanamycin) and cultured in the dark at 23° C. Those transferred to recovery media are cultured 10 days then transferred to selection media. They are maintained on selection media with mannitol for 14 days then transferred to selection media without mannitol, but still containing kanamycin 200 µg/ml. The cells are then subcultured in 3 week intervals for 6–8 weeks. For regeneration, the developing embryogenic tissue is isolated and transferred to MS medium (Murashige et al., *Physiol Plant* 15:473–497 (1962)) supplemented with 5 mg/L 6-benzyl-aminopurine for line H99 and 5 mg/L zeatin for line Pa91 and cultured at 23° C. for 10 to 14 days. The embryogenic tissue is then transferred to MS medium without hormones and 6% sucrose. Developing shoots are transferred to half-strength MS medium with 1.5% sucrose for further development into plantlets. The plantlets are transferred to soil and grown to maturity in the greenhouse.

Electroporation, Selection and Regeneration of Type I Callus

Developing type I callus of Pa91 is cultured for about 2 months on Mahi VII substrate (N6 medium (Chu et al., Sci. Sin. Peking 18, 659–668 (1975)), supplemented with 100 mg/L casein hydrolysate. 6 mM 1-proline, 0.5 g/L 2-(N-morpholino)ethanesulfonic acid (Mes), 1 mg/L 2,4-D, and 2% sucrose solidified with 1.6 g/L Phytage (Sigma), and supplemented with 0.75 g/L $MgCl_2$, pH 5.8) subcultured every 14 to 20 days. Embryogenic tissue is dissected from the developing type I callus and preconditioned by cutting in about 1.5 mm thick pieces in EPM buffer without KCl and preplasmolysis for about 3 hours in this buffer. The 150 mg of callus fragments are then transferred to cuvettes containing 200 µL of EPM supplemented with 80 mM KCl. Electroporation, selection and regeneration protocols are as described above for immature zygotic embryos.

Confirmation of Transformation of Callus

To show that callus lines grown on kanamycin selection medium have acquired the ADH or the ALDH gene, DNA is isolated from pieces of each kanamycin resistant callus line and from unselected control callus, employing the methods of Dellaporta et al., *Plant Mol. Biol. Rep.* 1(4):19–21 (1983). Southern blot is performed on restriction enzyme digested DNA according to standard protocols as disclosed by Maniatis, however using the radiolabelled human ADH and human ALDH as a probe. Polymerase chain reaction is performed on DNA using primers to amplify selected sections of the human ADH or human ALDH gene. Standard protocols are employed as disclosed by the Perkin Elmer PCR manual. This confirms integration of the human ADH or human ALDH gene into the maize genome.

Immunological assays or in situ hybridizations are performed on tissue from plants showing integration. Frozen sections are prepared and stained with antibodies directed against ADH and ALDH.

Extraction of ADH and ALDH

Progeny containing the desired ADH and ALDH is identified by electrophoresis or Elisa technology. After cultivation, the transgenic plants are harvested to recover the produced ADH and the produced ALDH using conventional methods. This harvesting step may consist of harvesting the entire plant, or only part of the plant commercially harvested.

Any processing of the corn kernels obtained from these transgenic maize must be done under carefully controlled conditions such that the temperature will not exceed about 41° C. for more than a few minutes. In this way, the enzymatic activity of the stomach ADH will be maintained in the corn.

There are two major milling processes for corn. Dry milling of corn separates the germ from the endosperm. The endosperm is recovered in the form of coarse grits, corn meal and corn flakes, or it may be passed through fine rollers and reduced to corn flour.

ADH and ALDH, respectively, may be extracted from the corn by means of an existing corn wet-milling process. In the wet-milling process, after the corn kernels are cleaned to remove coarse material such as dust, chaff, cobs, stones and insects, the corn is steeped in large tanks of warm water generally containing acid and sulfur dioxide (a sulfurous acid solution) to soften the corn and render the starch granules separable from the protein matrix that envelopes them. About 7% of the kernel's dry substance is leached out during this step, forming protein-rich steep water used as a feed ingredient. The softened kernels are coarsely ground to release the germs. The course grind produces a pulpy material containing germ, fiber (hull), starch protein and ADH or ALDH which is passed through a hydrocyclone separator where the germ is recovered. Because of their high oil content, the germs are lighter than the starch, protein, and fiber fractions and can easily be separated. The hulls and endosperm, the heavier particles, are discharged from the bottom of the hydrocyclone tube for further processing and the lighter germs are drawn off the top of the vortex. The germs are washed free of remaining starch, dried and the corn oil is removed by expelling or solvent extraction. The spent germs are used as a feed ingredient.

The slurry now contains the fiber (hulls) and the protein, starch and ADH or ALDH fractions of the endosperm. The starch-protein-fiber- ADH or ALDH slurry is subjected to an intense milling to release additional starch from the fiber.

The fiber is then wet-screened from the starch-protein slurry, washed free of starch, and carefully dried to form the major component of corn gluten feed. The best fiber can be additionally purified to become corn bran. The starch-protein- ADH or ALDH slurry is separated into its component parts by passing it through combinations of high speed centrifuges and hydrocyclones to separate the heavier starch from the lighter protein. The protein fraction is filtered and carefully dried in rotary or flash driers to yield corn gluten, which is rich in the corn protein known as zein. The starch slurry is dewatered and dried to produced corn starch, which may be used as such or further converted into corn syrup by the hydrolytic action of acid or starch-splitting enzymes. Known separation techniques, such as high speed centrifuge, are used to separate the ADH and ALDH fractions based on their respective molecular weight. The ADH and ALDH is dried and used in therapeutic and food supplement applications.

The presence of residual ADH and ALDH in the corn plant after extraction does not affect its use in animal feed because without the addition of NAD there is no or little enzyme activity in the plant. In addition to being biocompatible, forms of ADH and ALDH are already naturally present in corn and animals.

PACKAGING OF THE ADH/ALDH/NAD COMPOUND OF THE INVENTION

The ADH/ALDH compound of the invention is preferably administered orally in dosage unit formulations containing conventional non-toxic pharmaceutically acceptable carriers, diluents, adjuvants and vehicles in combination with NAD. If desired, it may contain other active ingredients. The compositions containing an ADH/ALDH/NAD compound according to the invention may be in a form suitable for oral use, for example, as tablets, troches, lozenges, aqueous or oily suspensions, dispersible powders or granules, emulsions, hard or soft capsules, syrups or elixirs.

The preferred route of administration is by oral administration, but may optionally be administered parenterally by subcutaneous injection, intravenous, intramuscular, intrasternal injection or by infusion. It is further contemplated that administration may be effected by inhalation or spray or rectally.

In addition to conventional drug administration methods, drug delivery means including implants, drug entrapment in small vesicles that are injected into the blood stream or within pumps or polymeric materials that are placed beneath the skin, for instance, or transdermal delivery via skin patches may be used. R. S. Geary et al., Drug Delivery Systems and Recombinant Proteins, *Biotechnology and Safety Assessments*, edited by J. A. Thomas and L. A. Myers, Raven Press, Ltd., pp. 79–95, New York, 1993.

Formulations intended for oral use may be prepared by known methods for manufacturing pharmaceuticals. Such formulations may contain one or more agents selected from the group consisting of sweetening, flavoring, coloring and preserving agents. Tablets typically contain the active ingredient mixed with non-toxic pharmaceutically acceptable excipients. Such excipients may include binding agents such as starch, gelatin or acacia; lubricating agents such as magnesium stearate, stearic acid or talc; inert diluents, such as calcium carbonate, sodium carbonate, lactose, calcium phosphate or sodium phosphate; granulating and disintegrating agents such as corn starch or alginic acid. The tablets may be uncoated or they may be coated using methods known in the art to delay disintegration and absorption in the gastrointestinal tract. Time delay materials such as glyceryl monostearate or glyceryl distearate may be used. Effectiveness of the composition may be enhanced in a slow-release formulation.

Compositions suitable for oral use include hard gelatin capsules where the active ingredient is mixed with an inert solid diluent such as calcium carbonate, calcium phosphate or kaolin, or soft gelatin capsules where the active ingredient is mixed with water or an oil medium such as liquid paraffin or olive or peanut oil.

Aqueous suspensions typically contain the active ingredient mixed with suitable excipients including suspending agents such as sodium carboxymethylcellulose. methylcellulose, hydroxypropylmethylcellulose, sodium alginate, polyvinylpyrrolidone, gum tragacanth and gum acacia; dispersing or wetting agents such as lecithin, polyoxyethylene stearate, heptadecaethyleneoxycetanol, polyoxyethylene sorbitol monooleate, or polyethylene sorbitain monooleate; and optionally one or more preservatives, coloring agents, flavoring agents, and sweetening agents, such as sucrose or saccharin, such as are well-known in the art.

Oily suspensions having the active ingredients suspended in a vegetable oil such as olive oil or coconut oil, or in a mineral oil such as liquid paraffin may contain thickening agents such as beeswax, hard paraffin or cetyl alcohol; sweetening and flavoring agents to improve palatability of the preparation; and preservatives such as ascorbic acid.

Dispersible powders and granules may be used to prepare aqueous suspensions by adding water so that the active ingredient is mixed with suitable dispersion or wetting agents, suspending agents, sweetening, flavoring and coloring agents, and one or more preservatives.

The composition of the invention may take the form of oil-in-water emulsions wherein the oily phase may be a vegetable oil such as olive oil, or a mineral oil such as liquid paraffin, or mixtures of these. Suitable emulsifying agents include naturally-occurring gums such as gum acacia or gum tragacanth, naturally-occurring phosphatides such as soybean and lecithin, and sorbitan monooleate and polyoxyethylene sorbitan monooleate. Sweetening and flavoring agents and preservatives may also be added.

Syrups and elixirs formulated with sweetening agents such as glycerol, propylene gycol, sorbitol or sucrose may also contain a demulcent, preservatives and flavoring and coloring agents.

The compositions may be in the form of a sterile injectable solution or suspension formulated in accordance with known methods using suitable dispersing or wetting agents, solvents and suspending agents. Suitable non-toxic parenterally acceptable diluents or solvents include water, Ringer's solution, isotonic sodium chloride solution, or sterile, fixed oils.

It must be realized that the amount of active ingredient to be combined with the carrier materials to produce a single dosage varies depending upon the particular method of administration, the amount of alcohol consumption, and the sex and origins (Oriental or non-Oriental) of the subject, among other factors. It is contemplated that subjects may take multiple doses of the composition in the event that substantially greater alcohol consumption occurs or is expected to occur. Excess composition than required to counter the effects of the alcohol consumed is not harmful; the excess is eliminated routinely from the system. Effective dosages to metabolize moderate to heavy social drinking in a short period of time are contemplated. More specifically, it is contemplated that dosages on the order of from about 100 to about 5000 FCC units, and preferably around about 3000 FCC units, may be ingested prior to alcohol consumption to counteract the effects of alcohol. FCC units are measurements of enzyme activity levels. An FCC (Food Chemical Codex) unit is that quantity of enzyme that will liberate one micromole of substrate per minute at 37° C. and pH 4.5.

It will be understood that the specific dosage for a particular subject depends upon a wide range of factors including the activity of the ADH/ALDH/NAD compound, the sex, age, body weight, diet and general physical and mental health of the individual, genetic factors, environmental influences, time and method of administration, combination with other drugs, rate of excretion, and the severity of the individual's drinking problem. The dose level may vary among individuals depending on their level of consumption of alcohol and the severity of their symptoms in reaction to alcohol.

While a number of embodiments of the present invention have been shown and described, it will be obvious to one skilled in the art that many changes and modifications may be made thereto without departing from the spirit and scope of the invention. It will be appreciated that the specific gene construct is not critical to the invention, and various other gene constructs that are the most suitable to particular hosts may be used.

We claim:

1. A composition comprising human class IV σ ADH and human ALDH2 in combination with nicotinamide adenine dinucleotide, said human class IV σ ADH and said ALDH2 produced from a source selected from the group consisting of plants, seeds, yeast and bacteria, wherein said composition metabolizes ethanol.

2. The composition of claim 1 further comprising an effective amount of a buffering agent.

3. The composition of claim 1 wherein said composition is packaged in a form selected from the group consisting of pills, capsules, powders, pastes and food products.

4. The composition of claim 2 wherein said composition is packaged in a form selected from the group consisting of pills, capsules, powders, pastes and food products.

5. The composition of claim 1 wherein said composition is packaged so as to retain its biological activity in the human stomach.

6. The composition of claim 3 wherein said composition is incorporated in liposome-type vesicles.

7. The composition of claim 5 wherein said composition is incorporated in a swollen gel.

8. A composition comprising human ALDH2 in combination with nicotinamide adenine dinucleotide, said human ALDH2 produced from a source selected from the group consisting of plants, seeds, yeast and bacteria, wherein said composition metabolizes ethanol.

9. The composition of claim 8 further comprising an effective amount of a buffering agent.

10. The composition of claim 8 wherein said composition is packaged in a form selected from the group consisting of pills, capsules, powders, pastes and food products.

11. The composition of claim 9 wherein said composition is packaged in a form selected from the group consisting of pills, capsules, powders, pastes and food products.

12. The composition of claim 8 wherein said composition is packaged so as to retain its biological activity in the human stomach.

13. The composition of claim 12 wherein said composition is incorporated in liposome-type vesicles.

14. The composition of claim 12 wherein said composition is incorporated in a swollen gel.

15. A method of facilitating the metabolism of ingested alcohol comprising ingesting an effective amount of the composition of claim 1 prior to consumption of alcohol.

16. A method of facilitating the metabolism of ingested alcohol comprising ingesting an effective amount of the composition of claim 2 prior to consumption of alcohol.

17. A method of facilitating the metabolism of ingested alcohol comprising ingesting an effective amount of the composition of claim 8 prior to consumption of alcohol.

18. A method of facilitating the metabolism of ingested alcohol comprising ingesting an effective amount of the composition of claim 9 prior to consumption of alcohol.

19. A composition comprising ADH and ALDH in combination with nicotinamide adenine dinucleotide, said ADH and said ALDH produced from a source selected from the group consisting of plants, seeds, yeast and bacteria, wherein the composition metabolizes ethanol.

20. The composition of claim 19 further comprising an effective amount of a buffering agent.

21. The composition of claim 19 wherein said composition is packaged in a form selected from the group consisting of pills, capsules, powders, pastes and food products.

22. The composition of claim 20 wherein said composition is packaged in a form selected from the group consisting of pills, capsules, powders, pastes and food products.

23. The composition of claim 19 wherein said composition is packaged so as to retain its biological activity in the human stomach.

\* \* \* \* \*